United States Patent
Knap et al.

(10) Patent No.: US 10,412,977 B2
(45) Date of Patent: Sep. 17, 2019

(54) USE OF BACTERIAL AMYLASES IN FEED FOR POULTRY

(71) Applicants: Novozymes A/S, Bagsvaerd (DK); DSM IP Assets B.V., Te Heerlen (NL)

(72) Inventors: Inge Knap, Basel (CH); Jose-Octavio Sorbara, Basel (CH); Rafael Gustavo Hermes, Basel (CH)

(73) Assignees: Novozymes A/S, Bagsvaerd (DK); DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 15/039,936

(22) PCT Filed: Dec. 1, 2014

(86) PCT No.: PCT/EP2014/076097
§ 371 (c)(1),
(2) Date: May 27, 2016

(87) PCT Pub. No.: WO2015/079063
PCT Pub. Date: Jun. 4, 2015

(65) Prior Publication Data
US 2017/0006895 A1    Jan. 12, 2017

(30) Foreign Application Priority Data

Nov. 29, 2013    (EP) .................................... 13194992

(51) Int. Cl.
| | |
|---|---|
| A61K 38/54 | (2006.01) |
| A23K 20/189 | (2016.01) |
| A23K 50/75 | (2016.01) |
| A23K 20/174 | (2016.01) |
| A23K 20/20 | (2016.01) |
| A61K 9/00 | (2006.01) |
| A61K 38/47 | (2006.01) |
| A61K 45/06 | (2006.01) |

(52) U.S. Cl.
CPC .......... *A23K 20/189* (2016.05); *A23K 20/174* (2016.05); *A23K 20/20* (2016.05); *A23K 50/75* (2016.05); *A61K 9/0056* (2013.01); *A61K 38/47* (2013.01); *A61K 45/06* (2013.01); *C12Y 302/01001* (2013.01)

(58) Field of Classification Search
None
See application file for complete search history.

(56) References Cited

U.S. PATENT DOCUMENTS

| | | |
|---|---|---|
| 3,250,622 A | 5/1966 | Brooks et al. |
| 2011/0183032 A1 | 7/2011 | Duan et al. |
| 2013/0171296 A1 | 7/2013 | Isaksen |

FOREIGN PATENT DOCUMENTS

| | | |
|---|---|---|
| WO | 01/41795 A1 | 6/2001 |
| WO | 03/068256 A1 | 8/2003 |
| WO | 2008/006881 A1 | 1/2008 |

OTHER PUBLICATIONS

DaSilva et al., GenBank Accession No. AAB86961.1, Nov. 1997.*
Gracia et al., Poultry Science, vol. 82, pp. 436-442 (2003).
Gracia et al., Animal Feed Science and Technology, vol. 150, No. 3-4, pp. 303-315 (2009).
Onderci et al., Poultry Science, vol. 85, pp. 505-510 (2006).
Rojo et al., Animal Feed Science and Technology, vol. 123-124, pp. 655-665 (2005).
Tricarico et al., Animal Science, vol. 81, pp. 365-374 (2005).

* cited by examiner

*Primary Examiner* — Richard G Hutson
(74) *Attorney, Agent, or Firm* — Elias Lambiris

(57) ABSTRACT

The present invention relates to methods and uses of at least one bacterial amylase in poultry feed to improve the nutritional value of the feed. The invention also relates to poultry feed and poultry feed additives comprising at least one bacterial amylase and at least one vitamin and/or mineral which improve the nutritional value of the feed.

8 Claims, No Drawings

Specification includes a Sequence Listing.

USE OF BACTERIAL AMYLASES IN FEED FOR POULTRY

CROSS-REFERENCE TO RELATED APPLICATIONS

This application is a 35 U.S.C. 371 national application of international application no. PCT/EP2014/076097 filed Dec. 1, 2014, which claims priority or the benefit under 35 U.S.C. 119 of European application no. 13194992.7 filed Nov. 29, 2013. The content of these applications is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to methods and uses of at least one bacterial amylase in poultry feed to improve the nutritional value of the feed. The invention also relates to poultry feed and poultry feed additives comprising at least one bacterial amylase and at least one vitamin and/or mineral which improve the nutritional value of the feed.

Description of the Related Art

WO 03/068256 A1 describes an amylase feed supplement for improved ruminant nutrition. The amylase used is a fungal amylase produced by *Aspergillus oryzae*. Tricarico et al, in Animal Science 2005, 81: 365-374, describe the effects of *Aspergillus oryzae* extract containing alpha-amylase activity on ruminal fermentation and milk production in lactating Holstein cows.

U.S. Pat. No. 3,250,622 discloses the use of a specific additive containing proteolytic and amylolytic enzymes as well as gumase, intimately associated with a ground malt carrier, for stimulating milk production in dairy cows. The enzyme source is not specified.

Rojo et al (Animal Feed Science and Technology, 123-124 (2005), 655-665) studied the effects of exogenous amylases from *Bacillus licheniformis* and *Aspergillus niger* on ruminal starch digestion and lamb performance.

WO 01/41795 A1 relates to the use of a combination of a protease and an inner salt of a quaternary amine carboxylic acid in the treatment and/or prophylaxis of coccidiosis and bacterial infections. An alpha-amylase is an optional enzyme which may be added.

Gracia et al (Animal Feed Sci Tech, 150:3-4, (2009), 303-315) showed that a multi-enzyme complex with xylanase, protease and alpha-amylase activity improved body weight gain and FCR in broilers aged 1-4 days.

It is an object of the present invention to provide alternative, preferably improved, amylases which improve feed utilization and/or weight gain in poultry.

SUMMARY OF THE INVENTION

The present invention relates to the use of at least one bacterial amylase in poultry feed to improve the nutritional value of the feed, wherein the bacterial amylase is a polypeptide having at least 80% identity to amino acids 1-481 of SEQ ID NO: 2.

The invention also relates to a method for improving the nutritional value of poultry feed, the method comprising the step of adding at least one bacterial amylase to the feed, wherein the bacterial amylase is a polypeptide having at least 80% identity to amino acids 1-481 of SEQ ID NO: 2.

The invention furthermore relates to a poultry feed additive comprising at least one bacterial amylase, together with (i) at least one vitamin, (ii) at least one mineral, or (iii) at least one vitamin and at least one mineral, wherein the bacterial amylase is a polypeptide having at least 80% identity to amino acids 1-481 of SEQ ID NO: 2 as well as poultry feed comprising the poultry feed additive and 10 w %-40 w % soybean meal.

Definitions

Amylase: In the present context, an amylase is an enzyme that catalyzes the endohydrolysis of starch and other linear and branched oligo- and polysaccharides. In a particular embodiment, the amylase for use according to the invention has alpha-amylase activity, viz. catalyzes the endohydrolysis of 1,4-alpha-glucosidic linkages in oligosaccharides and polysaccharides. Alpha-amylases act, e.g., on starch, glycogen and related polysaccharides and oligosaccharides in a random manner, liberating reducing groups in the alpha-configuration.

Amylases belong to the EC 3.2.1.-group, such as EC 3.2.1.1 (alpha-amylase, 1,4-alpha-D-glucan glucanohydrolase), EC 3.2.1.2 (beta-amylase), EC 3.2.1.3 (glucan 1,4-alpha-glucosidase, amyloglucosidase, or glucoamylase), EC 3.2.1.20 (alpha-glucosidase), EC 3.2.1.60 (glucan 1,4-alpha-maltotetraohydrolase), EC 3.2.1.68 (isoamylase), EC 3.2.1.98 (glucan 1,4-alpha-maltohexosidase), or EC 3.2.1.133 (glucan 1,4-alpha-maltohydrolase). The amylase of the invention is an alpha-amylase belonging to the group EC 3.2.1.1. The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. http://www.chem.qmw.ac.uk/iubmb/enzyme/index.html.

Amylase activity may be determined by any suitable assay. Generally, assay-pH and assay-temperature may be adapted to the enzyme in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Preferred pH values and temperatures are in the physiological range, such as pH values of 3, 4, 5, 6, 7, or 8, and temperatures of 30, 35, 37, or 40° C. A preferred assay is the reducing sugar assay of Example 4 herein. Alternatively, the following amylase assay can be used: Substrate: Phadebas tablets (Pharmacia Diagnostics; cross-linked, insoluble, blue-coloured starch polymer, which is mixed with Poultry serum albumin and a buffer substance, and manufactured into tablets). Assay Temperature: 37° C. Assay pH: 4.3 (or 7.0, if desired). Reaction time: 20 min. After suspension in water the starch is hydrolyzed by the alpha-amylase, giving soluble blue fragments. The absorbance of the resulting blue solution, measured at 620 nm, is a function of the alpha-amylase activity. One Fungal alpha-Amylase Unit (1 FAU) is the amount of enzyme which breaks down 5.26 g starch per hour at the standard assay conditions. A preferred starch is Merck, Amylum soluble Erg. B. 6, Batch 9947275. A more detailed assay description, APTSMYQI-3207, is available on request from Novozymes A/S, Krogshoejvej 36, DK-2880 Bagsvaerd, Denmark.

Concentrates: The term "concentrates" means feed with high protein and energy concentrations, such as fish meal, molasses, oligosaccharides, sorghum, seeds and grains (either whole or prepared by crushing, milling, etc from e.g. corn, oats, rye, barley, wheat), oilseed press cake (e.g. from cottonseed, safflower, sunflower, soybean, rapeseed/canola, peanut or groundnut), palm kernel cake, yeast derived material and distillers grains (such as wet distillers grains (WDS) and dried distillers grains with solubles (DDGS)).

Feed Conversion Ratio: The term "feed conversion ratio" (FCR) is indicative of how effectively a feed is utilized. The lower the FCR, the better the feed is utilized. The FCR may be determined on the basis of an animal trial comprising a first treatment in which the amylase for use according to the invention is added to the animal feed in a desired concentration (e.g., 100 to 400 mg enzyme protein per kg feed) and a second treatment (control) with no addition of the amylase to the animal feed. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%. In further particular embodiments, the FCR is improved (i.e. reduced) as compared to the control by at least 2.6%, 2.7%, 2.8%, 2.9%, or at least 3.0%. In still further particular embodiments, the FCR is improved (i.e., reduced) as compared to the control by at least 3.1%, 3.2%, 3.3%, 3.4%, 3.5%, 3.6%, 3.7%, or at least 3.8%.

Poultry: The term "poultry" means domesticated birds kept by humans for the eggs they produce and/or their meat and/or their feathers. Poultry includes broilers and layers. Poultry include members of the superorder Galloanserae (fowl), especially the order Galliformes (which includes chickens, Guinea fowls, quails and turkeys) and the family Anatidae, in order Anseriformes, commonly known as "waterfowl" and including domestic ducks and domestic geese. Poultry also includes other birds that are killed for their meat, such as the young of pigeons. Examples of poultry include chickens (including layers, broilers and chicks), ducks, geese, pigeons (including but not limited to squab), Guinea fowl, turkeys and quail.

Poultry Feed: The term "poultry feed" means a feed which is given to poultry, such as chickens (including layers, broilers and chicks), ducks, geese, pigeons (including but not limited to squab), Guinea fowl, turkeys and quail. Poultry feed often comprises a premix which is added to e.g. concentrate and then fed to the poultry.

Poultry Feed additive: The term "poultry feed additive" means a premix comprising e.g. vitamins and/or minerals. Premixes are recognized terms in the art for certain feed additives. They may be solid or liquid. For example, a trace mineral premix is a composition which is intended for addition to animal feed and which comprises desired kinds and amounts of trace minerals. A vitamin premix is a composition which is intended for addition to animal feed and which comprises desired kinds and amounts of vitamins. Some premixes include both vitamins and trace minerals and optionally formulating agents, preservatives, antibiotics, other feed ingredients or any combination thereof which is mixed with feed high in protein and/or energy (such as concentrates) before being given to the poultry.

Sequence Identity: The relatedness between two amino acid sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the—nobrief option) is used as the percent identity and is calculated as follows:

(Identical Residues×100)/(Length of Alignment−
Total Number of Gaps in Alignment)

Weight gain: The term "weight gain" means how much weight an animal has gained during a certain period of time. An improved weight gain means an improved daily, weekly, bi-weekly, or monthly weight gain (in g or kg per the relevant time period), relative to a control without added amylase. This is preferably determined in a trial as described in the above FCR-paragraph.

DETAILED DESCRIPTION OF THE INVENTION

It has been surprisingly found that adding an amylase to poultry feed improves the nutritional value of the feed. If the apparent metabolisable energy (AME) of the poultry feed is reduced by 100 kcal/kg, then the body weight gain and FCR of poultry worsens compared to poultry on a standard diet. However, the inventors have surprisingly found that including the amylase of the invention in this reduced AME diet improves the body weight gain and FCR of the poultry.

Thus in a first aspect, the invention relates to method for improving the nutritional value of poultry feed, the method comprising the step of adding at least one bacterial amylase to the feed, wherein the bacterial amylase is a polypeptide having at least 80% identity to amino acids 1-481 of SEQ ID NO: 2. In an embodiment, the bacterial amylase is a polypeptide having at least 85% identity to amino acids 1-481 of SEQ ID NO: 2. In an embodiment, the bacterial amylase is a polypeptide having at least 90% identity to amino acids 1-481 of SEQ ID NO: 2. In an embodiment, the bacterial amylase is a polypeptide having at least 91% identity to amino acids 1-481 of SEQ ID NO: 2. In an embodiment, the bacterial amylase is a polypeptide having at least 92% identity to amino acids 1-481 of SEQ ID NO: 2. In an embodiment, the bacterial amylase is a polypeptide having at least 93% identity to amino acids 1-481 of SEQ ID NO: 2. In an embodiment, the bacterial amylase is a polypeptide having at least 94% identity to amino acids 1-481 of SEQ ID NO: 2. In an embodiment, the bacterial amylase is a polypeptide having at least 95% identity to amino acids 1-481 of SEQ ID NO: 2. In an embodiment, the bacterial amylase is a polypeptide having at least 96% identity to amino acids 1-481 of SEQ ID NO: 2. In an embodiment, the bacterial amylase is a polypeptide having at least 97% identity to amino acids 1-481 of SEQ ID NO: 2. In an embodiment, the bacterial amylase is a polypeptide having at least 98% identity to amino acids 1-481 of SEQ ID NO: 2. In an embodiment, the bacterial amylase is a polypeptide having at least 99% identity to amino acids 1-481 of SEQ ID NO: 2. In an embodiment, the polypeptide comprises or consists of amino acids 1-481 of SEQ ID NO: 2.

In a further aspect of the first aspect of the invention, the invention relates to method for improving the nutritional value of poultry feed, the method comprising the step of adding at least one bacterial amylase to the feed, wherein the bacterial amylase is a polypeptide having at least 80% identity to amino acids 1-481 of SEQ ID NO: 2 and wherein the bacterial amylase improves the weight gain and/or feed conversion ratio of poultry. In an embodiment, the bacterial amylase is a polypeptide having at least 85% identity to amino acids 1-481 of SEQ ID NO: 2. In an embodiment, the bacterial amylase is a polypeptide having at least 90% identity to amino acids 1-481 of SEQ ID NO: 2. In an embodiment, the bacterial amylase is a polypeptide having at least 91% identity to amino acids 1-481 of SEQ ID NO: 2. In an embodiment, the bacterial amylase is a polypeptide having at least 92% identity to amino acids 1-481 of SEQ ID NO: 2. In an embodiment, the bacterial amylase is a polypeptide having at least 93% identity to amino acids 1-481 of SEQ ID NO: 2. In an embodiment, the bacterial amylase is a polypeptide having at least 94% identity to amino acids 1-481 of SEQ ID NO: 2. In an embodiment, the bacterial amylase is a polypeptide having at least 95% identity to amino acids 1-481 of SEQ ID NO: 2. In an embodiment, the bacterial amylase is a polypeptide having at least 96% identity to amino acids 1-481 of SEQ ID NO: 2. In an embodiment, the bacterial amylase is a polypeptide having at least 97% identity to amino acids 1-481 of SEQ ID NO: 2. In an embodiment, the bacterial amylase is a polypeptide having at least 98% identity to amino acids 1-481 of SEQ ID NO: 2. In an embodiment, the bacterial amylase is a polypeptide having at least 99% identity to amino acids 1-481 of SEQ ID NO: 2. In an embodiment, the polypeptide comprises or consists of amino acids 1-481 of SEQ ID NO: 2.

In an embodiment of the first aspect, the bacterial amylase improves the feed conversion ratio. In an embodiment, the bacterial amylase improves the body weight gain. In a further embodiment, the bacterial amylase improves the feed conversion ratio and improves the body weight gain. In a preferred embodiment, the bacterial amylase improves the feed conversion ratio of poultry in a diet wherein the poultry feed has reduced apparent metabolisable energy compared to a standard poultry feed. In a preferred embodiment, the bacterial amylase improves the body weight gain of poultry in a diet wherein the poultry feed has reduced apparent metabolisable energy compared to a standard poultry feed. In a preferred embodiment, the bacterial amylase improves the feed conversion ratio and body weight gain of poultry in a diet wherein the poultry feed has reduced apparent metabolisable energy compared to a standard poultry feed.

In a further embodiment of the first aspect of the invention, the poultry feed has reduced apparent metabolisable energy compared to a standard poultry feed. In an embodiment, the apparent metabolisable energy is between 85% and 99.9% of a standard poultry feed, such as between 90% and 99.5%, between 91% and 99%, between 92% and 99%, between 93% and 98.5%, or between 94% and 98% of a standard poultry feed, wherein the energy of a standard poultry feed is 3050 kcal/kg for days 1-21 and 3170 kcal/kg for days 22-40.

In a further embodiment of the first aspect of the invention, the bacterial amylase is added to the poultry feed at a dose of between 0.01 and 200 mg enzyme protein per kg diet, such as 0.05-100, 0.1-50, 0.2-35, 0.4-20, 0.5-25, 0.6-15, 0.8-8, 1-10 or 1-6.mg enzyme protein/kg. In a further embodiment of the first aspect of the invention, the bacterial amylase is added to the poultry feed at a dose of between 1 and 5000 KNU/kg feed, such as 5-2500, 10-1000, 15-600, 20-400, 25-300, 30-200, 40-160 KNU/kg feed.

In a second aspect, the invention relates to method for improving the nutritional value of poultry feed, the method comprising the step of adding at least one bacterial amylase to the feed, wherein the bacterial amylase is a polypeptide having at least 80% identity to amino acids 1-481 of SEQ ID NO: 2. In an embodiment, the bacterial amylase is a polypeptide having at least 85% identity to amino acids 1-481 of SEQ ID NO: 2. In an embodiment, the bacterial amylase is a polypeptide having at least 90% identity to amino acids 1-481 of SEQ ID NO: 2. In an embodiment, the bacterial amylase is a polypeptide having at least 91% identity to amino acids 1-481 of SEQ ID NO: 2. In an embodiment, the bacterial amylase is a polypeptide having at least 92% identity to amino acids 1-481 of SEQ ID NO: 2. In an embodiment, the bacterial amylase is a polypeptide having at least 93% identity to amino acids 1-481 of SEQ ID NO: 2. In an embodiment, the bacterial amylase is a polypeptide having at least 94% identity to amino acids 1-481 of SEQ ID NO: 2. In an embodiment, the bacterial amylase is a polypeptide having at least 95% identity to amino acids 1-481 of SEQ ID NO: 2. In an embodiment, the bacterial amylase is a polypeptide having at least 96% identity to amino acids 1-481 of SEQ ID NO: 2. In an embodiment, the bacterial amylase is a polypeptide having at least 97% identity to amino acids 1-481 of SEQ ID NO: 2. In an embodiment, the bacterial amylase is a polypeptide having at least 98% identity to amino acids 1-481 of SEQ ID NO: 2. In an embodiment, the bacterial amylase is a polypeptide having at least 99% identity to amino acids 1-481 of SEQ ID NO: 2. In an embodiment, the polypeptide comprises or consists of amino acids 1-481 of SEQ ID NO: 2.

In a further aspect of the second aspect of the invention, the invention relates to method for improving the nutritional value of poultry feed, the method comprising the step of adding at least one bacterial amylase to the feed, wherein the bacterial amylase is a polypeptide having at least 80% identity to amino acids 1-481 of SEQ ID NO: 2 and wherein the bacterial amylase improves the weight gain and/or feed conversion ratio of poultry. In an embodiment, the bacterial amylase is a polypeptide having at least 85% identity to amino acids 1-481 of SEQ ID NO: 2. In an embodiment, the bacterial amylase is a polypeptide having at least 90% identity to amino acids 1-481 of SEQ ID NO: 2. In an embodiment, the bacterial amylase is a polypeptide having at least 91% identity to amino acids 1-481 of SEQ ID NO: 2. In an embodiment, the bacterial amylase is a polypeptide having at least 92% identity to amino acids 1-481 of SEQ ID NO: 2. In an embodiment, the bacterial amylase is a polypeptide having at least 93% identity to amino acids 1-481 of SEQ ID NO: 2. In an embodiment, the bacterial amylase is a polypeptide having at least 94% identity to amino acids 1-481 of SEQ ID NO: 2. In an embodiment, the bacterial amylase is a polypeptide having at least 95% identity to amino acids 1-481 of SEQ ID NO: 2. In an embodiment, the bacterial amylase is a polypeptide having at least 96% identity to amino acids 1-481 of SEQ ID NO: 2. In an embodiment, the bacterial amylase is a polypeptide having at least 97% identity to amino acids 1-481 of SEQ ID NO: 2. In an embodiment, the bacterial amylase is a polypeptide having at least 98% identity to amino acids 1-481 of SEQ ID NO: 2. In an embodiment, the bacterial amylase is a polypeptide having at least 99% identity to amino acids 1-481 of SEQ ID NO: 2. In an embodiment, the polypeptide comprises or consists of amino acids 1-481 of SEQ ID NO: 2.

In an embodiment of the second aspect, the bacterial amylase improves the feed conversion ratio. In an embodiment, the bacterial amylase improves the body weight gain. In a further embodiment, the bacterial amylase improves the feed conversion ratio and improves the body weight gain. In a preferred embodiment, the bacterial amylase improves the feed conversion ratio of poultry in a diet wherein the poultry feed has reduced apparent metabolisable energy compared to a standard poultry feed. In a preferred embodiment, the bacterial amylase improves the body weight gain of poultry in a diet wherein the poultry feed has reduced apparent metabolisable energy compared to a standard poultry feed. In a preferred embodiment, the bacterial amylase improves the feed conversion ratio and body weight gain of poultry in a diet wherein the poultry feed has reduced apparent metabolisable energy compared to a standard poultry feed.

In a further embodiment of the second aspect of the invention, the poultry feed has reduced apparent metabolisable energy compared to a standard poultry feed. In an embodiment, the apparent metabolisable energy is between 85% and 99.9% of a standard poultry feed, such as between 90% and 99.5%, between 91% and 99%, between 92% and 99%, between 93% and 98.5%, or between 94% and 98% of a standard poultry feed, wherein the energy of a standard poultry feed is 3050 kcal/kg for days 1-21 and 3170 kcal/kg for days 22-40.

In a further embodiment of the second aspect of the invention, the bacterial amylase is added to the poultry feed at a dose of between 0.01 and 200 mg enzyme protein per kg diet, such as 0.05-100, 0.1-50, 0.2-35, 0.4-20, 0.5-25, 0.6-15, 0.8-8, 1-10 or 1-6.mg enzyme protein/kg. In a further embodiment of the first aspect of the invention, the bacterial amylase is added to the poultry feed at a dose of between 1 and 5000 KNU/kg feed, such as 5-2500, 10-1000, 15-600, 20-400, 25-300, 30-200, 40-160 KNU/kg feed.

In a second aspect, the invention relates to a poultry feed additive comprising at least one bacterial amylase, together with (i) at least one vitamin, (ii) at least one mineral, or (iii) at least one vitamin and at least one mineral, wherein the bacterial amylase is a polypeptide having at least 80% identity to amino acids 1-481 of SEQ ID NO: 2. In an embodiment, the bacterial amylase is a polypeptide having at least 85% identity to amino acids 1-481 of SEQ ID NO: 2. In an embodiment, the bacterial amylase is a polypeptide having at least 90% identity to amino acids 1-481 of SEQ ID NO: 2. In an embodiment, the bacterial amylase is a polypeptide having at least 91% identity to amino acids 1-481 of SEQ ID NO: 2. In an embodiment, the bacterial amylase is a polypeptide having at least 92% identity to amino acids 1-481 of SEQ ID NO: 2. In an embodiment, the bacterial amylase is a polypeptide having at least 93% identity to amino acids 1-481 of SEQ ID NO: 2. In an embodiment, the bacterial amylase is a polypeptide having at least 94% identity to amino acids 1-481 of SEQ ID NO: 2. In an embodiment, the bacterial amylase is a polypeptide having at least 95% identity to amino acids 1-481 of SEQ ID NO: 2. In an embodiment, the bacterial amylase is a polypeptide having at least 96% identity to amino acids 1-481 of SEQ ID NO: 2. In an embodiment, the bacterial amylase is a polypeptide having at least 97% identity to amino acids 1-481 of SEQ ID NO: 2. In an embodiment, the bacterial amylase is a polypeptide having at least 98% identity to amino acids 1-481 of SEQ ID NO: 2. In an embodiment, the bacterial amylase is a polypeptide having at least 99% identity to amino acids 1-481 of SEQ ID NO: 2. In an embodiment, the polypeptide comprises or consists of amino acids 1-481 of SEQ ID NO: 2. In a preferred embodiment, the poultry feed additive improves the nutritional value of a poultry feed.

In an embodiment of the third aspect of the invention, the invention relates to a poultry feed additive comprising at least one bacterial amylase, together with (i) at least one vitamin, (ii) at least one mineral, or (iii) at least one vitamin and at least one mineral, wherein the bacterial amylase is a polypeptide having at least 80% identity to amino acids 1-481 of SEQ ID NO: 2 and wherein poultry feed additive improves the weight gain or feed conversion ratio of poultry. In an embodiment, the bacterial amylase is a polypeptide having at least 85% identity to amino acids 1-481 of SEQ ID NO: 2. In an embodiment, the bacterial amylase is a polypeptide having at least 90% identity to amino acids 1-481 of SEQ ID NO: 2. In an embodiment, the bacterial amylase is a polypeptide having at least 91% identity to amino acids 1-481 of SEQ ID NO: 2. In an embodiment, the bacterial amylase is a polypeptide having at least 92% identity to amino acids 1-481 of SEQ ID NO: 2. In an embodiment, the bacterial amylase is a polypeptide having at least 93% identity to amino acids 1-481 of SEQ ID NO: 2. In an embodiment, the bacterial amylase is a polypeptide having at least 94% identity to amino acids 1-481 of SEQ ID NO: 2. In an embodiment, the bacterial amylase is a polypeptide having at least 95% identity to amino acids 1-481 of SEQ ID NO: 2. In an embodiment, the bacterial amylase is a polypeptide having at least 96% identity to amino acids 1-481 of SEQ ID NO: 2. In an embodiment, the bacterial amylase is a polypeptide having at least 97% identity to amino acids 1-481 of SEQ ID NO: 2. In an embodiment, the bacterial amylase is a polypeptide having at least 98% identity to amino acids 1-481 of SEQ ID NO: 2. In an embodiment, the bacterial amylase is a polypeptide having at least 99% identity to amino acids 1-481 of SEQ ID NO: 2. In an embodiment, the polypeptide comprises or consists of amino acids 1-481 of SEQ ID NO: 2. In a preferred embodiment, the poultry feed additive improves the nutritional value of a poultry feed.

In a fourth aspect, the invention relates to a poultry feed comprising the poultry feed additive of the third aspect and 10 w %-40 w % soybean meal. In a preferred embodiment, the poultry feed comprising the poultry feed additive of the third aspect and 10 w %-40 w % soybean meal improves the feed conversion ratio of poultry. In a preferred embodiment, the poultry feed comprising the poultry feed additive of the third aspect and 10 w %-40 w % soybean meal improves the weight gain of poultry. In a preferred embodiment, the poultry feed comprising the poultry feed additive of the third aspect and 10 w %-40 w % soybean meal improves the weight gain and/or feed conversion ratio of poultry.

In an embodiment of the fourth aspect, the bacterial amylase improves the feed conversion ratio. In an embodiment, the bacterial amylase improves the body weight gain. In a further embodiment, the bacterial amylase improves the feed conversion ratio and improves the body weight gain. In a preferred embodiment, the bacterial amylase improves the feed conversion ratio of poultry in a diet wherein the poultry feed has reduced apparent metabolisable energy compared to a standard poultry feed. In a preferred embodiment, the bacterial amylase improves the body weight gain of poultry in a diet wherein the poultry feed has reduced apparent metabolisable energy compared to a standard poultry feed. In a preferred embodiment, the bacterial amylase improves the feed conversion ratio and body weight gain of poultry in a diet wherein the poultry feed has reduced apparent metabolisable energy compared to a standard poultry feed.

In a further embodiment of the fourth aspect of the invention, the poultry feed has a reduced apparent metabolisable energy compared to a standard poultry feed. In an embodiment, the apparent metabolisable energy is between 85% and 99.9% of a standard poultry feed, such as between 90% and 99.5%, between 91% and 99%, between 92% and 99%, between 93% and 98.5%, or between 94% and 98% of a standard poultry feed, wherein the energy of a standard poultry feed is 3050 kcal/kg for days 1-21 and 3170 kcal/kg for days 22-40.

In a further embodiment of the fourth aspect of the invention, the bacterial amylase is added to the poultry feed at a dose of between 0.01 and 200 mg enzyme protein per kg diet, such as 0.05-100, 0.1-50, 0.2-35, 0.4-20, 0.5-25, 0.6-15, 0.8-8, 1-10 or 1-6.mg enzyme protein/kg. In a further embodiment of the first aspect of the invention, the bacterial amylase is added to the poultry feed at a dose of between 1 and 5000 KNU/kg feed, such as 5-2500, 10-1000, 15-600, 20-400, 25-300, 30-200, 40-160 KNU/kg feed.

In a particular embodiment, the amylase, in the form in which it is added to the feed, or when being included in a feed additive, is well-defined. Well-defined means, that the amylase preparation is at least 50% pure on a protein-basis. In other particular embodiments the amylase preparation is at least 60, 70, 80, 85, 88, 90, 92, 94, or at least 95% pure. Purity may be determined by any method known in the art, e.g. by SDS-PAGE, or by Size-exclusion chromatography (see Example 12 of WO 01/58275).

A well-defined amylase preparation is advantageous. For instance, it is much easier to dose correctly to the feed an amylase that is essentially free from interfering or contaminating other enzymes. The term dose correctly refers in particular to the objective of obtaining consistent and constant results, and the capability of optimising dosage based upon the desired effect.

Amylase preparations with purities of this order of magnitude are in particular obtainable using recombinant methods of production, whereas they are not so easily obtained and also subject to a much higher batch-to-batch variation when produced by traditional fermentation methods.

The bacterial amylase for use according to the invention is included in Poultry diets or Poultry feed additives in an effective amount. It is presently contemplated that an effective amount is below 400 mg enzyme protein per kg diet dry matter, preferably below 350, 300, 250, 200, 150, 100 or below 50 mg enzyme protein per kg diet dry matter (ppm). On the other hand, an effective amount may be above 0.01 mg enzyme protein per kg diet dry matter, preferably above 0.5, 0.10, 0.15, 0.20, 0.25, 0.30, 0.35, 0.40, 0.45, 0.50, 0.75 or above 1 mg enzyme protein per kg diet dry matter (ppm). Accordingly, non-limiting examples of preferred dose ranges are: 0.01-200 mg enzyme protein/kg, preferably 0.05-100, 0.1-50, 0.5-25 or 1-10 mg enzyme protein/kg. Additional examples of preferred dosage ranges, all in mg enzyme protein/kg, are: 0.2-35, 0.4-20, 0.6-15, 0.8-8, and 1-6. In other non-limiting examples, the preferred dose ranges of the bacterial amylase of the invention are between 1 and 5000 KNU/kg feed, such as 5-2500, 10-1000, 15-600, 20-400, 25-300, 30-200, 40-160 KNU/kg feed.

For determining mg amylase protein per kg feed, the amylase is purified from the feed composition, and the specific activity of the purified amylase is determined using the desired amylase assay. The amylase activity of the feed composition as such is also determined using the same assay, and on the basis of these two determinations, the dosage in mg amylase enzyme protein per kg feed is calculated.

The same principles apply for determining mg amylase protein in feed additives. Of course, if a sample is available of the amylase used for preparing the feed additive or the feed, the specific activity is determined from this sample (no need to purify the amylase from the feed composition or the additive).

For a taxonomical classification and identification of bacteria reference is made to Bergey's Manual of Systematic Bacteriology (1986), vol 2, ISBNO-683-0783. In the alternative, the well-known 16SrRNA sequence analysis can be used (see e.g. Johansen et al, Int. J. Syst. Bacteriol, 1999, 49, 1231-1240, in particular the Methods section on p. 1233, $2^{nd}$ column); or taxonomy experts can be consulted, e.g. from DSMZ or other recognized depositary institutes.

As employed herein the term bacterial designates amylases that are derived from bacteria. The term "derived from" includes enzymes obtainable, or obtained, from wild type bacterial strains, as well as variants thereof. The variants may have at least one substitution, insertion, and/or deletion of at least one amino acid residue. The term variant also includes shufflants, hybrids, chimeric enzymes and consensus enzymes. The variants may have been produced by any method known in the art, such as site-directed mutagenesis, random mutagenesis, consensus derivation processes (EP 897985), and gene shuffling (WO 95/22625, WO 96/00343), etc. For the present purposes an amylase variant qualifies as bacterial when at least one bacterial amylase has been used for its design, derivation or preparation. The term bacterial does not refer to a potential recombinant production host but only to the origin of the amylase encoding gene that is hosted by it.

The amylase for use according to the invention is preferably derived from a strain of *Bacillus*, such as strains of *Bacillus amyloliquefaciens, Bacillus circulans, Bacillus halmapalus, Bacillus licheniformis, Bacillus megaterium, Bacillus* sp., *Bacillus stearothermophilus*, and *Bacillus subtilis*; preferably from strains of *Bacillus amyloliquefaciens, Bacillus halmapalus, Bacillus licheniformis, Bacillus* sp., *Bacillus subtilis*, and *Bacillus stearothermophilus*.

Examples of wildtype amylases are those derived from *Bacillus licheniformis*, such as Swissprot entry name AMY_BACLI, primary accession number P06278 (SEQ ID NO: 8), and the commercial amylase sold by Novozymes A/S under the tradename of DURAMYL; *Bacillus amyloliquefaciens*, such as Swissprot entry name AMY_BACAM, primary accession number P00692 (SEQ ID NO: 7), and the commercial amylase sold by Novozymes A/S under the tradename of BAN; *Bacillus megaterium*, such as Swissprot entry name AMY_BACME, primary accession number P20845; *Bacillus circulans*, such as Swissprot entry name AMY_BACCI, primary accession number P08137; *Bacillus stearothermophilus*, such as Swissprot entry name AMY_BACST, primary accession number P06279 (SEQ ID NO: 9), and the commercial amylase sold by Novozymes A/S under the tradename of TERMAMYL SC. Another example is from *Bacillus subtilis*, such as Swissprot entry name AMY_BACSU, primary accession number P00691.

Examples of amylases contained in commercial products are: BAN, Stainzyme, Termamyl SC, Natalase, and Duramyl (all from Novozymes), and in the Validase BAA and Validase HT products (from Valley Research). Further particular examples of amylases for use according to the invention are the amylases contained in the following commercial products: Clarase, DexLo, GC 262 SP, G-Zyme G990, G-Zyme G995, G-Zyme G997, G-Zyme G998, HTAA, Optimax 7525, Purastar OxAm, Purastar ST, Spezyme AA, Spezyme Alpha, Spezyme BBA, Spezyme Delta AA, Spezyme DBA, Spezyme Ethyl, Spezyme Fred (GC521), Spezyme HPA, and Ultraphlow (all from Genencor); Validase HT340L, Valley Thin 340L (all from Valley Research); Avizyme 1500, Dextro 300 L, Kleistase, Maltazyme, Maxamyl, Thermozyme, Thermatex, Starzyme HT 120 L, Starzyme Super Conc, and Ultraphlo.

Additional non-limiting examples of amylases are:

Amylases having, comprising or consisting of amino acids 1-481, 1-484, 1-486, or 1-513 of SEQ ID NO: 2 (where "1" refers to the starting amino acid of the mature peptide, Ala, cf. the sequence listing);

Amylases having, comprising or consisting of amino acids 1-483 of SEQ ID NO: 4;

Amylases having, comprising or consisting of amino acids 1-483 of SEQ ID NO: 5;

Amylases having, comprising or consisting of amino acids 1-481 of SEQ ID NO: 6 (where "1" refers to the starting amino acid of the mature peptide, Val, cf. the sequence listing);

Amylases having, comprising or consisting of amino acids 1-483 of SEQ ID NO: 7 (where "1" refers to the starting amino acid of the mature peptide, Val cf. the sequence listing);

Amylases having, comprising or consisting of amino acids 1-483 of SEQ ID NO: 8 (where "1" refers to the starting amino acid of the mature peptide, Ala, cf. the sequence listing); and Amylases having, comprising or consisting of amino acids 1-515 of SEQ ID NO: 9 (where "1" refers to the starting amino acid of the mature peptide, Ala, cf. the sequence listing);

as well as fragments or variants of any of the above specified amylases which retain amylase activity.

A fragment is a polypeptide having one or more amino acids deleted from the amino and/or carboxyl terminus. Preferably, a fragment contains at least 450 amino acid residues, more preferably at least 460 amino acid residues, even more preferably at least 470 amino acid residues, and most preferably at least 480 amino acid residues. Additional preferred fragments contain at least 481, 483, 484, or at least 513 amino acid residues. Examples of enzymatically active fragments of the amylase of SEQ ID NO: 2 are the sequences having amino acids 1-481, 1-484, and 1-486 thereof.

In a particular embodiment, the amylase for use according to the invention is pelleting stable, and/or thermostable. The melting temperature (Tm) of an enzyme is a measure of its thermostability. The amylase of the invention may have a Tm of at least 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C. or at least 95° C., as determined by Differential Scanning Calorimetry (DSC). The DSC is performed in a 10 mM sodium phosphate, 50 mM sodium chloride buffer, pH 7.0. The scan rate is constant, e.g. 1.5° C./min. The interval scanned may be from 20 to 100° C. Another buffer may be selected for the scanning, e.g. a buffer of pH 5.0, 5.5, 6.0, or pH 6.5. In further alternative embodiments, a higher or lower scan rate may be used, e.g. a lower one of 1.4° C./min, 1.3° C./min, 1.2° C./min, 1.1° C./min, 1.0° C./min, or 0.9° C./min.

In another preferred embodiment, the amylase for use according to the invention has an activity at pH 7.0 and 37° C. of at least 35% relative to the activity at the pH-optimum and 37° C. More preferably, the activity at pH 7.0 and 37° C. is at least 40, 45, 50, 55, 60, 65, 70, or at least 75% of the activity at the pH-optimum and 37° C. (cf. Table 1 of Example 2).

In another preferred embodiment, the amylase of the invention has an activity at pH 7.0 and 37° C. and in the presence of 5 mM bile salts of at least 25% relative to the activity at the pH-optimum and 37° C. in the absence of bile salts. More preferably, the activity at pH 7.0 and 37° C. and in the presence of 5 mM bile salts is at least 30, 35, 40, 45, 50, 55, 60, or at least 65% of the activity at the pH-optimum and 37° C. in the absence of bile salts (cf. Table 2 of Example 2).

In a still further preferred embodiment, the specific activity of the amylase of the invention, at pH 7.0 and 37° C., is at least 10%, more preferably at least 15, 20, 25, 30, 35, 40, 45, 50, 55, 60, 65, or at least 70%, relative to the specific activity of the amylase of TERMAMYL SC at pH 5.0 and 37° C. (cf. Table 3 of Example 2).

In another preferred embodiment, the specific activity of the amylase of the invention, at pH 7.0 and 37° C. and in the presence of 5 mM bile salts, is at least 10%, more preferably at least 15, 20, 25, 30, 35, 40, 45, 50, 55, 60, 65, 70, or at least 75%, relative to the specific activity of the amylase of TERMAMYL SC at pH 5.0 and 37° C. and in the presence of 5 mM bile salts (cf. Table 4 of Example 2).

The activities referred to in the above preferred embodiments may suitably be determined using a reducing sugar assay, e.g. as described in Example 2, using preferably waxy corn as a substrate. A detailed procedure is described in Example 2.

In another particular embodiment, the amylase for use according to the invention is stable in the presence of protease. Examples of proteases are digestive proteases, and feed proteases such as the proteases described in, e.g., WO 01/58275, WO 01/58276, WO 2004/111220 2004/111221, WO 2004/072221, and WO 2005/035747. Examples of digestive proteases are pancreatin and pepsin. The protease stability may be determined by incubating 0.5 mg purified amylase enzyme protein/ml in a buffer at a desired pH (e.g. pH 2, 3, 4, or 5), for the desired time (e.g. 30, 45, 60, 90, or 120 minutes) in the presence of protease (e.g. pepsin, 70 mg/l), and then raising pH to the desired pH (e.g. pH 4, 5, 6, or 7) and measuring residual activity using e.g. the reducing sugar assay of Example 2 herein. The residual amylase activity is preferably at least 20%, preferably at least 30, 40, 50, 60, 70, 80, or at least 90% relative to the control (a non-protease-treated sample).

Poultry Feed and Poultry Feed Additives

The present invention also relates to poultry feed and poultry feed additives comprising the amylase of the present invention. Preferably, the poultry feed or poultry feed additive are enriched in the amylase of the invention. The term "enriched" indicates that the amylase activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In an embodiment, the poultry feed or poultry feed additive comprises the polypeptide of the invention and one or more formulating agents. In an embodiment, the poultry feed or poultry feed additive comprises the polypeptide of the invention together with (i) at least one vitamin, (ii) at least one mineral, or (iii) at least one vitamin and at least one mineral. In an embodiment, the poultry feed or poultry feed additive comprises the polypeptide of the invention together with one or more formulating agents and (i) at least one vitamin, (ii) at least one mineral, or (iii) at least one vitamin and at least one mineral. In an embodiment, the poultry feed or poultry feed additive further comprises one or more amino acids. In an embodiment, the poultry feed or poultry feed additive further comprises one or more other feed ingredients. In an embodiment, the poultry feed or poultry feed additive further comprises one or more amino acids and one or more other feed ingredients.

In an embodiment, the poultry feed additive consists of the polypeptide of the invention and one or more components from the group consisting of vitamins, minerals, formulating agents and other feed ingredients. In an embodiment, the poultry feed additive consists of the polypeptide of the invention, one or more vitamins and one or more formulating agents. In an embodiment, the poultry feed additive consists of the polypeptide of the invention, one or more minerals and one or more formulating agents. In an embodiment, the poultry feed additive consists of the polypeptide of the invention, one or more minerals, one or more vitamins and one or more formulating agents. In an embodiment, the poultry feed additive consists of the polypeptide of the invention, one or more minerals, one or more vitamins, one or more other feed ingredients and one or more formulating agents.

In an embodiment, the poultry feed consists of the polypeptide of the invention, one or more concentrates and one or more components from the group consisting of vitamins, minerals, formulating agents and other feed ingredients. In an embodiment, the poultry feed consists of the polypeptide of the invention, one or more concentrates, one or more vitamins and one or more formulating agents. In an embodiment, the poultry feed consists of the polypeptide of the invention, one or more concentrates, one or more minerals and one or more formulating agents. In an embodiment, the poultry feed consists of the polypeptide of the invention, one or more concentrates, one or more minerals, one or more vitamins and one or more formulating agents. In an embodiment, the poultry feed consists of the polypeptide of the invention, one or more concentrates, one or more minerals, one or more vitamins, one or more other feed ingredients and one or more formulating agents.

The poultry feed has a crude protein content of 50-800 g/kg, and furthermore comprises at least one amylase as claimed herein.

The final poultry feed compositions according to the invention comprises, in addition to the amylase for use according to the invention as described hereinabove, at least soybean meal and a trace mineral and/or vitamin premix as specified above. For example the feed composition contains 10 w %-40 w % soybean meal and 0.5 w %-2 w % of trace minerals and vitamins.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In preferred examples, the poultry feed composition contains per kg of feed: vit. A, 7,000-9,000 UI; vit. D3, 2,000-2,500 UI; vit. E, 15-20 mg; vit. K3, 1, 5-2.5 mg; thiamine, 1-2 mg; riboflavin, 6-7 mg; pyridoxine, 2-3 mg; panthothenic acid, 10-12 mg; folic acid, 0.5-1.5 mg; biotin, 0.1-1 mg; iron, 100-150 mg; zinc, 100-150 mg; manganese, 100-150 mg; cobalt, 1-2 mg; copper, 10-20 mg.

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the European Table of Energy Values for Poultry Feed-stuffs, Spelderholt centre for poultry research and extension, 7361 DA Beekbergen, The Netherlands. Grafisch bedrijf Ponsen & Iooijen bv, Wageningen. ISBN 90-71463-12-5.

The poultry feed of the invention may also contain animal protein, such as Meat and Bone Meal, Feather meal, and/or Fish Meal, typically in an amount of 0-25%. The poultry feed of the invention may also comprise Dried Distillers Grains with Solubles (DDGS), typically in amounts of 0-30%.

In still further particular embodiments, the poultry feed of the invention contains 0-80% maize; and/or 0-80% sorghum; and/or 0-70% wheat; and/or 0-70% Barley; and/or 0-30% oats; and/or 10-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Formulating Agent

The poultry feed additive of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the poultry feed additive is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol.

For a solid formulation, the formulation may be for example as a granule, spray dried powder or agglomerate. The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In an embodiment, the solid poultry feed additive is in granulated form. The granule may have a matrix structure where the components are mixed homogeneously. However, the granule typically comprises a core particle and one or more coatings, which typically are salt and/or wax coatings. The core particle can either be a homogeneous blend of amylase of the invention and optionally together with one or more salts or an inert particle with the amylase of the invention applied onto it.

In an embodiment, the material of the core particles are selected from the group consisting of inorganic salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals.

The salt coating is typically at least 1 μm thick and can either be one particular salt or a mixture of salts, such as $Na_2SO_4$, $K_2SO_4$, $MgSO_4$ and/or sodium citrate. Other examples are those described in e.g. WO 2008/017659, WO 2006/034710, WO 1997/05245, WO 1998/54980, WO 1998/55599, WO 2000/70034 or polymer coating such as described in WO 2001/00042.

In another embodiment, the poultry feed additive is a solid composition comprising the amylase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate and calcium carbonate. In a preferred embodiment, the solid composition is in granulated form. In an embodiment, the solid composition is in granulated form and comprises a core particle, an enzyme layer comprising the amylase of the invention and a salt coating.

In a further embodiment, the formulating agent is selected from one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: 1, 2-propylene glycol, 1, 3-propylene glycol, sodium sulfate, dextrin, cellulose, sodium thiosulfate and calcium carbonate.

Vitamins and Minerals

In another embodiment, the poultry feed or poultry feed additive may include one or more vitamins, such as one or more fat-soluble vitamins and/or one or more water-soluble vitamins. In another embodiment, the poultry feed or poultry feed additive may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

Amino Acids

The composition of the invention may further comprise one or more amino acids. Examples of amino acids which are used in animal feed are lysine, alanine, beta-alanine, threonine, methionine and tryptophan.

Other Feed Ingredients

The poultry feed or poultry feed additive comprising the amylase of the invention may further comprise colouring agents, stabilisers, growth improving additives and aroma compounds/flavourings, polyunsaturated fatty acids (PUFAs); reactive oxygen generating species, anti-microbial peptides and anti-fungal polypeptides.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are 018, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The present invention is further described by the following examples which should not be construed as limiting the scope of the invention.

EXAMPLES

Example 1: Alpha-Amylase Activity

Alpha-amylase activity was measured using the AMYL-kit which is commercially available from Roche Diagnostics, Cat.No. 11876473. The substrate is 4,6-ethylidene($G_7$)-p-nitrophenyl($G_1$)-alpha,D-maltoheptaoside (ethylidene-$G_7$PNP). The alpha-amylase splits off Ethylidene-$G_n$ and the resulting $G_n$-p-nitrophenyl is then cleaved by the enzyme alpha-glucosidase (part of the kit) under formation of glucose and the yellow-coloured p-nitrophenol.

The rate of formation of p-nitrophenol, which is a measure of the reaction rate and thereby of the alpha-amylase activity, is observed at 405 nm, e.g. by a Konelab 30 Analyzer (commercially available from Thermo Electron Corporation), e.g. using a measuring time of 2 min.

The reaction conditions are: Temperature 37° C., pH: 7.0, reaction time: 5 min. Calcium chloride 0.03M with Brij 0.0025% (Sigma B 4184) is preferably used as a stabilizer. The alpha-amylase activity may be given relative to a standard, e.g. in the units of KNU(S) which are determined relative to an alpha-amylase standard of a declared KNU(S) activity.

A more detailed assay description (EB-SM-0221.02) as well as a KNU(S) TERMAMYL SC standard is available on request from Novozymes A/S, Krogshoejvej 36, DK-2880 Bagsvaerd.

Example 2: Amylase pH Profiles, with and without Bile Salts

This experiment serves to determine the pH profiles of three alpha-amylases, two bacterial amylases of the invention and a prior art fungal *Aspergillus oryzae* amylase, with and without added bile salts.

The amylases used were a purified *Bacillus stearothermophilus* amylase variant (from TERMAMYL SC), a purified *Bacillus* sp. amylase variant (from STAINZYME), and, for comparison, a purified *Aspergillus oryzae* amylase (from FUNGAMYL). These enzyme preparations are all commercially available from Novozymes A/S, Krogshoejvej 36, DK-2880 Bagsvaerd, Denmark.

Reducing Sugar Assay

Enzyme buffer: 50 mM acetate, 50 mM imidazole, 50 mM malonic acid, 1 mM $CaCl_2$, 0.01% Triton X-100. Adjust to pH 2.0, 3.0, 4.0, 5.0, 6.0, or 7.0 with HCl/NaOH.

Substrate buffer: 1.5 mg/ml amylopectin (waxy corn, e.g. Waxy corn 04201 from Cerestar, batch WM5671), 50 mM acetate, 50 mM imidazole, 50 mM malonic acid, 1 mM $CaCl_2$. Adjust to the desired pH (as above) with HCl/NaOH. Incubate for 5 min at 100° C. The substrate buffer was made with or without 5 mM bile salts (i.e. Sodium taurocholate commercially available from e.g. LGC promochem, 500 g/mol).

The amylase activity was detected by reducing sugar assay. Briefly, 50 μl enzyme (diluted in enzyme buffer so as to fall within the linear range of the assay) was mixed with 100 μl substrate buffer in PCR-MTP (Thermo-Fast 96, ABgene, cat. no. AB-0600). The MTP's were incubated at 37° C. for 15 min, following which 75 μl stop solution (100 mM p-hydroxybenzoic acid hydrazide, 180 mM K—Na-tartrate, 2% NaOH) was added, and the plates were incubated at 95° C. for 10 min. Then 150 μl from each well was transferred to 96-well MTP, and the absorbance at 410 nm was monitored as a measure of amylase activity.

The results (average of duplicate determinations) are shown in Tables 1-4, below. Table 1 shows the activity of each enzyme at the pH indicated in the absence of bile salts. For each enzyme, the maximum activity was set to 100%. Table 2 shows the same as Table 1, but in the presence of 5 mM bile salts. Table 3 shows the activity of each enzyme per mg enzyme protein at the pH indicated in the absence of bile salts, relative to the maximum enzyme activity measured in this experiment, which was the activity of the TERMAMYL SC enzyme at pH 5.0 (100%). The activity of each enzyme has accordingly been normalized relative to this activity. The amount of enzyme protein for each enzyme was determined on the basis of the specific activity. Table 4 shows the same as Table 3, but in the presence of 5 mM bile salts. Here the activity of the TERMAMYL SC enzyme at pH 5.0 in the presence of 5 mM bile salts is the reference value (100%).

TABLE 1

Relative activity without bile salts

| Enzyme | pH | | | | | |
|---|---|---|---|---|---|---|
| | 2 | 3 | 4 | 5 | 6 | 7 |
| FUNGAMYL | 0.0 | 0.0 | 77.4 | 93.4 | 100.0 | 25.6 |
| STAINZYME | 0.3 | 0.8 | 2.8 | 22.2 | 79.7 | 100.0 |
| TERMAMYL SC | 0.1 | 1.8 | 29.4 | 100.0 | 86.0 | 71.1 |

TABLE 2

Relative activity with bile salts

| Enzyme | pH | | | | | |
|---|---|---|---|---|---|---|
| | 2 | 3 | 4 | 5 | 6 | 7 |
| FUNGAMYL | 0.0 | 0.0 | 53.5 | 71.8 | 68.6 | 16.1 |
| STAINZYME | 0.0 | 0.0 | 0.8 | 2.5 | 61.4 | 78.1 |
| TERMAMYL SC | 0.0 | 0.0 | 10.4* | 76.0 | 68.6 | 59.7 |

*One measurement discarded for being clearly erroneous

TABLE 3

Normalized absolute activities relative to TERMAMYL SC without bile salts

| Enzyme | pH | | | | | |
|---|---|---|---|---|---|---|
| | 2 | 3 | 4 | 5 | 6 | 7 |
| FUNGAMYL | 0.0 | 0.0 | 10.9 | 13.2 | 14.1 | 3.6 |
| STAINZYME | 0.1 | 0.4 | 1.4 | 10.7 | 38.3 | 48.0 |
| TERMAMYL SC | 0.1 | 1.8 | 29.4 | 100.0 | 86.0 | 71.1 |

TABLE 4

Normalized absolute activities relative to TERMAMYL SC, with bile salts

| Enzyme | pH | | | | | |
|---|---|---|---|---|---|---|
| | 2 | 3 | 4 | 5 | 6 | 7 |
| FUNGAMYL | 0.0 | 0.0 | 9.9 | 13.3 | 12.7 | 3.0 |
| STAINZYME | 0.0 | 0.0 | 0.5 | 1.6 | 38.8 | 49.3 |
| TERMAMYL SC | 0.0 | 0.0 | 13.7 | 100.0 | 90.2 | 78.6 |

These results show that although bile salts seem to slightly reduce the amylase activity, the activity in the presence of 5 mM bile salts is still satisfactory. The results also show that bile salts do not lead to a shift of the pH optimum.

The results furthermore show that each of the *Bacillus* amylases of the invention all have more than 50% relative activity at pH 7, which is not the case for the comparative fungal amylase.

Finally, Tables 3 and 4 demonstrate that, at least under these conditions, the amylase from TERMAMYL SC has a significantly higher activity per mg enzyme than the other two amylases tested.

Example 3: A Broiler Chicken Feed ("Starter")

A broiler chicken feed ("starter") containing a mixture of compounds according to the invention can be prepared by mixing the following ingredients together using a conventional mixing apparatus at room temperature.

| Ingredient | Amount (kg) |
| --- | --- |
| Soybean meal | 34.50 |
| Maize | 20.00 |
| Wheat | 37.80 |
| Soy oil | 3.13 |
| Minerals | 2.90 |
| Synthetic amino acids premix | 0.17 |
| Vitamins and trace elements premix | 1.00 |
| Alpha amylase | 40-160 KNU/kg feed |

Example 4: A Broiler Chicken Feed ("Grower")

A broiler chicken feed ("grower") containing a mixture of compounds according to the invention can be prepared by mixing the following ingredients together using a conventional mixing apparatus at room temperature.

| Ingredients | Amount (kg) |
| --- | --- |
| Soybean meal | 31.20 |
| Maize | 20.00 |
| Wheat | 41.30 |
| Soy oil | 3.40 |
| Minerals | 2.50 |
| Synthetic amino acids premix | 0.10 |
| Vitamins and trace elements premix | 1.00 |
| Alpha amylase | 40-160 KNU/kg feed |

Example 5: Apparent Metabolisable Energy of Diets

An in vivo trail was carried out for the live performance of broilers which have been fed with basal diets as specified in Example 3 and 4 based on soybean meal and supplemented with TERMAMYL SC.

The study was carried out with a basal diet and with a corn/soy diet containing a replacement of 40% soybean meal with corn. In the trial TERMAMYL SC was used at graded inclusions of 40 KNU/kg feed, 80 KNU/kg feed, 120 KNU/kg feed and 160 KNU/kg feed.

TABLE 5

Outline of experimental treatments (Treatments with 9 replicates of 7 birds per cage)

| Treatment | Description |
| --- | --- |
| T1 | Basal diet |
| T2 | 60% Basal diet + 40% corn diet (soybean meal replaced by corn) |
| T3 | T1 + 40 KNU/kg feed RZ TERMAMYL SC |
| T4 | T1 + 80 KNU/kg feed RZ TERMAMYL SC |
| T5 | T1 + 120 KNU/kg feed RZ TERMAMYL SC |
| T6 | T1 + 160 KNU/kg feed RZ TERMAMYL SC |
| T7 | T2 + 40 KNU/kg feed RZ TERMAMYL SC |
| T8 | T2 + 80 KNU/kg feed RZ TERMAMYL SC |
| T9 | T2 + 120 KNU/kg feed RZ TERMAMYL SC |
| T10 | T2 + 160 KNU/kg feed RZ TERMAMYL SC |

Animals

The total number of 630 birds was delivered as day-old Cobb 500 male chicks. For trial the treatment groups was assigned to the metal cages using a completely randomized design comprising 10 treatments with 9 replicates per treatment (7 birds each).

Housing

The experiment was conducted at UFPR's experimental facilities. Treatment number displayed at the cages or pens, replicate number and treatment group must be visible at each pen. Maximum number of birds per pen and space per bird were in accordance with current legislation. Feed and water were supplied for ad libitum consumption. The birds were housed in metal cages equipped with gutter drinkers and feeders. The temperature and lighting regime were in accordance with broiler's recommendation. All pens were checked for sick and dead birds on a daily basis. Identification number, pens, age and body weight of each dead bird were recorded on a pen record sheet. General health status, weight, mortality and cause of death and filling grade as well as morphologic alterations/symptoms of the dead birds were recorded.

Measurements

The animals consumed the same diet until 14 days of age and thereafter experimental diet was formulated by adding acid insoluble ash (AIA) as a marker, using both based Rostagno et al. (2011). After the experimental diet adaptation period, the excreta sampling was held for four days (21 to 24 days) by the partial collection method. There were two collections per day, once in the morning and another in the late afternoon, approximately 9:00 am and 17:30 respectively, with plastic spatulas, avoiding collecting excreta near the cage nearby, the trough and drinkers. Then the samples were placed in a freezer and right after sampling, it was cleaned the remaining excreta to prevent contamination of the next sampling. Subsequently, the fecal samples were dried in a forced ventilation oven at 65° C. until constant weight.

The chicks were fasted for two hours, and ate for 1 hour and a half to the digestive tract were filled for ileal digestibility mesuration. The birds were slaughtered by cervical dislocation and ileal content was taken in 4 cm below the Meckel diverticulum and 4 cm above the ileocecal junction. The content samples were instantly frozen in liquid nitrogen and then stored in the freezer. Subsequently, lyophilization of the content was performed.

Diets, excreta and ileal contents were analyzed for dry matter (DM), crude protein (CP), gross energy (GE), fat (F) and acid insoluble ash (AIA). Before calculating the metabolisable and digestibility, the data were corrected for dry matter (DM 105° C.), then metabolisable and digestible and metabolisable energy by the method of partial collection was calculated using insoluble ash acid (AIA) as a marker. The digestibility calculation was made according to the following equation: digestibility=100−(100*(% in diet marker/marker feces %)*(% feces nutrient/dietary nutrient %)).

After calculating the diet coefficient of digestibility and metabolizable, we calculated the digestibility of corn according to Matterson et al. (1965) by the following formula: CD ingredient=CD Ref+((CD Inclusion 40−CD Ref %)/(% inclusion of corn MS*)).

Statistical Analysis

The data was analysed by the study investigator and mortality was considered in data analysis. Statistical analysis of apparent metabolisable energy and digestibility parameters were performed according to standard least squares procedures appropriate for the study design and the characteristics of the data set and comprising outlier check.

Results

The data was valued the most suitable for biological interpretation. When the results were not satisfactory for linear regression, the data was analyzed by method of regression Linear Plato for the best enzymatic response. The results are summarized in table 6.

TABLE 6

Apparent metabolisable energy (AME) of the diets, diets with corn and corn with different levels of TERMAMYL SC.

| Levels (Amylase KNU/kg feed) | | AME diets | AME diets with corn |
|---|---|---|---|
| | 0 | 3711 | 3705 |
| | 40 | 3736 | 3750 |
| | 80 | 3775 | 3843 |
| | 120 | 3779 | 3875 |
| | 160 | 3762 | 3846 |
| P | Linear | 0.0167 | <0.0001 |
| | Quadratic | 0.0951 | 0.0043 |
| | RLP | 0.0552 | 0.0383* |
| | Contrast | 0.1833 | <0.0001 |

*I = 3860 r = 158
**I = 4023 r = 183;
I = maximum AME r = optimum level

The results show that adding the alpha-amylase of the invention into the poultry feed improved the apparent metabolisable energy of the diets, and especially the diet where 40% soybean meal was replaced by corn.

Example 6: Animal Trial in Chicken

A second in vivo trial was carried out for the live performance of broilers which have been fed with basal diets as specified below.

The study is an investigation of the supplementation effects of Termamyl SC (bacterial alpha-amylase, IUB No. 3.2.1.1.) on broiler performance using a model with a corn/soy diet.

Performance parameters were done weekly and from 1 to 7, 1 to 14, 1 to 21 d, 1 to 28, 1 to 35 d, 1 to 40 d and 22 to 40 d.

TABLE 7

Outline of experimental treatments

| Treatment | Description | 1 to 21 d, kcal/kg AME | 22 to 40 d, kcal/kg |
|---|---|---|---|
| T1 | −100 kcal/kg | 2.950 | 3.070 |
| T2* | −50 kcal/kg | 3.000 | 3.120 |
| T3* | Usual levels | 3.050 | 3.170 |

TABLE 7-continued

Outline of experimental treatments

| Treatment | Description | 1 to 21 d, kcal/kg AME | 22 to 40 d, kcal/kg |
|---|---|---|---|
| T4* | +50 kcal/kg | 3.100 | 3.220 |
| T5 | +100 kcal/kg | 3.150 | 3.270 |
| T6 | Trt 1 + Amylase | 2.950 | 3.070 |

*Treatments T2, T3 and T4 were obtained by mixing the diets T1 and T5.
Amylase: Termamyl SC (SEQ ID NO: 2), 80 KNU/kg feed

TABLE 8

Ingredients composition

| Composition (as DM), % | Corn | Soybean meal |
|---|---|---|
| Dry matter, % | 87.70 | 88.24 |
| Crude Protein | 7.84 | 47.01 |
| Ether extract | 3.32 | 1.31 |
| Crude Fiber | 0.88 | 3.92 |
| Ash | 1.11 | 5.46 |
| Calcium | 0.04 | 0.34 |
| Phosphorus | 0.25 | 0.67 |
| Dig. Arg | 0.343 | 3.249 |
| Dig. Cys | 0.240 | 1.932 |
| Dig. His | 0.869 | 3.259 |
| Dig. Ile | 0.203 | 2.676 |
| Dig. Leu | 0.145 | 0.583 |
| Dig. Lys | 0.334 | 2.209 |
| Dig. Met + Cys | 0.239 | 1.631 |
| Dig. Met | 0.307 | 1.992 |
| Dig. Phe | 0.211 | 1.170 |
| Dig. Thr | 0.297 | 1.180 |
| Dig. Trp | 0.054 | 0.585 |
| Dig. Val | 0.343 | 3.249 |

[1]Determined using NIR.

TABLE 9

Estimated composition of the basal diets

| | Starter diet (1 to 21 d) | | Finisher diet (22 to 40 d) | |
|---|---|---|---|---|
| Ingredients | T1 | T5 | T1 | T5 |
| Corn | 53.65 | 54.12 | 57.72 | 58.37 |
| Soybean Meal | 37.90 | 37.81 | 33.10 | 33.00 |
| Soybean Oil | 2.57 | 4.69 | 3.66 | 5.71 |
| Dicalcium Phosphate | 0.87 | 0.87 | 0.56 | 0.56 |
| Limestone | 1.33 | 1.33 | 1.18 | 1.18 |
| Salt | 0.47 | 0.47 | 0.45 | 0.45 |
| DL-Methionine 99.9% | 0.27 | 0.27 | 0.24 | 0.24 |
| L-Lysine HCl 76% | 0.14 | 0.14 | 0.17 | 0.17 |
| L-Threonine 98.5% | 0.04 | 0.04 | 0.04 | 0.04 |
| Choline Chloride 60% | 0.08 | 0.08 | 0.10 | 0.10 |
| Min. & Vit. Premix[1] | 0.15 | 0.15 | 0.15 | 0.15 |
| Kaolin | 2.50 | 0.00 | 2.60 | 0.00 |
| Avilamycin | 0.01 | 0.01 | 0.01 | 0.01 |
| Monensin | 0.01 | 0.01 | 0.01 | 0.01 |
| RONOZYME HiPhos 1,000 FYT/kg | 0.01 | 0.01 | 0.01 | 0.01 |
| Total | 100.00 | 100.00 | 100.00 | 100.00 |
| Nutrients, % | | | | |
| AME (kcal/kg)[2] | 2.950 | 3.150 | 3.070 | 3.270 |
| Crude protein | 22.386 | 22.376 | 20.406 | 20.416 |
| Calcium | 0.889 | 0.891 | 0.761 | 0.760 |
| Av. P. | 0.440 | 0.440 | 0.371 | 0.371 |
| Total P | 0.520 | 0.521 | 0.459 | 0.460 |
| Sodium | 0.202 | 0.202 | 0.202 | 0.198 |
| Potassium | 0.846 | 0.845 | 0.865 | 0.864 |
| Chloride | 0.352 | 0.352 | 0.359 | 0.354 |

TABLE 9-continued

Estimated composition of the basal diets

| Ingredients | Starter diet (1 to 21 d) | | Finisher diet (22 to 40 d) | |
| --- | --- | --- | --- | --- |
| | T1 | T5 | T1 | T5 |
| Ether extract | 5.169 | 7.285 | 5.940 | 7.990 |
| Crude Fiber | 2.402 | 2.407 | 2.227 | 2.234 |
| Lys dig. | 1.229 | 1.227 | 1.128 | 1.131 |
| Met + Cys dig. | 0.896 | 0.897 | 0.825 | 0.826 |
| Thr dig. | 0.788 | 0.786 | 0.723 | 0.723 |
| Trp dig. | 0.238 | 0.238 | 0.214 | 0.214 |
| Arg dig. | 1.411 | 1.409 | 1.268 | 1.267 |
| Val dig. | 0.931 | 0.931 | 0.847 | 0.847 |
| Ile dig. | 0.895 | 0.894 | 0.807 | 0.806 |

[1] Composition per kg of feed: vit. A, 9,000 UI; vit. D3, 2,500 UI; vit. E, 20 mg; vit. K3, 2.5 mg; thiamine, 2 mg; riboflavin, 6 mg; pyridoxine, 3 mg; cyanocobalamine, 0.015 mg, panthothenic acid, 12 mg; niacin, 35 mg; folic acid, 1.5 mg; biotin, 0.1 mg; iron, 100 mg; zinc, 130 mg; manganese, 130 mg; cobalt, 2 mg; copper, 20 mg; iodine, 2 mg; selenium, 0.25 mg.
[2] Apparent Metabolisable Energy.

Birds and Housing

A total number of 1,800 one-day-old male Cobb×Cobb 500 slow feathering chicks was used. Treatment groups were assigned to floor pens using a completely randomized arrangement comprising 8 treatments with 9 replicates and 25 birds per replication.

Feed and water were supplied for ad libitum consumption. Environmental temperature was controlled to maintain bird comfort with the use of an infrared heating lamp. Ambient temperature was adjusted to 32° C. on the first day, being reduced by 1° C. every two days until comfort temperature is reached. Birds were placed on rice hulls bedding.

Experimental Diets

All diets were produced in a 400 kg capacity mixer. Mixers were cleaned and vacuumed between each batch of feed. Diets were provided as mash. The chemical composition of corn and soybean meal was analyzed before the study begins.

Experimental Design

The design was completely randomized with 8 treatments and 9 replications of 25 birds each.

Measured Responses

Body weight, Body weight gain and feed conversion were evaluated at 7, 14, 21, 28, 35 and 40 days of age. Feed conversion was calculated as corrected for the weight of dead birds. Responses were recorded on a form individually available at each box.

Statistical Analysis

The study investigator analyzed data. Statistical analysis was performed following an appropriated procedure (SAS Institute, 2009).

Results

TABLE 10

Body weight gain of broilers fed diets with enzymes from 1 to 40 days of age, g

| Treatments | 1-7 d | 8-14 d | 15-21 d | 22-28 d | 29-35 d | 36-40 d |
| --- | --- | --- | --- | --- | --- | --- |
| −100 kcal/kg AME (Control diet) | 135 | 256$^d$ | 587$^b$ | 646 | 784 | 481 |
| −50 kcal/kg AME | 137 | 267$^{abc}$ | 589$^b$ | 641 | 785 | 488 |
| Usual levels | 138 | 265$^{bcd}$ | 602$^{ab}$ | 664 | 797 | 488 |
| +50 kcal/kg AME | 141 | 272$^{ab}$ | 604$^{ab}$ | 660 | 796 | 493 |
| +100 kcal/kg AME | 144 | 277$^a$ | 611$^a$ | 664 | 815 | 501 |
| Control diet + amylase | 138 | 263$^{bcd}$ | 595$^{ab}$ | 672 | 801 | 493 |
| Mean | 138 | 266 | 597 | 656 | 798 | 493 |
| CV, % | 5.13 | 2.71 | 2.67 | 4.93 | 5.88 | 7.44 |
| Probability | 0.1245 | 0.0001 | 0.0423 | 0.4306 | 0.7798 | 0.9454 |

$^{a-d}$Means with different superscript letters differ significantly ($P < 0.05$) - Tukey test.

TABLE 11

Feed conversion rate of broilers fed diets with enzymes from 1 to 40 days of age, g:g

| Treatments | 1-7 d | 8-14 d | 15-21 d | 22-28 d | 29-35 d | 36-40 d |
| --- | --- | --- | --- | --- | --- | --- |
| −100 kcal/kg AME (Control diet) | 1.166$^a$ | 1.391$^a$ | 1.338$^a$ | 1.405$^a$ | 1.696 | 1.984 |
| −50 kcal/kg AME | 1.152$^{ab}$ | 1.290$^{ab}$ | 1.340$^a$ | 1.400$^{ab}$ | 1.675 | 1.891 |
| Usual levels | 1.167$^a$ | 1.298$^{ab}$ | 1.304$^{bc}$ | 1.363$^{abc}$ | 1.650 | 1.888 |
| +50 kcal/kg AME | 1.078$^{ab}$ | 1.265$^b$ | 1.291$^{cd}$ | 1.357$^{bc}$ | 1.649 | 1.864 |
| +100 kcal/kg AME | 1.037$^b$ | 1.248$^b$ | 1.270$^d$ | 1.334$^c$ | 1.652 | 1.857 |
| Control diet + amylase | 1.149$^{ab}$ | 1.305$^{ab}$ | 1.332$^{ab}$ | 1.387$^{ab}$ | 1.676 | 1.887 |
| Mean | 1.128 | 1.302 | 1.318 | 1.375 | 1.667 | 1.889 |
| CV, % | 7.77 | 5.27 | 1.51 | 2.31 | 4.10 | 5.22 |
| Probability | 0.0074 | 0.0037 | 0.0001 | 0.0002 | 0.8167 | 0.1855 |

$^{a-d}$Means with different superscript letters differ significantly ($P < 0.05$) - Tukey test.

TABLE 12

Cumulative body weight gain from 1 to 40 days of age, g

| Treatments | 1-7 d | 1-14 d | 1-21 d | 1-28 d | 1-35 d | 1-40 d |
|---|---|---|---|---|---|---|
| −100 kcal/kg AME (Control diet) | 135 | 391$^c$ | 978$^c$ | 1,624$^b$ | 2,409$^b$ | 2,889$^b$ |
| −50 kcal/kg AME | 137 | 403$^{bc}$ | 995$^{bc}$ | 1,625$^b$ | 2,417$^{ab}$ | 2,897$^b$ |
| Usual levels | 138 | 403$^{bc}$ | 1,006$^{ab}$ | 1,670$^{ab}$ | 2,449$^{ab}$ | 2,925$^{ab}$ |
| +50 kcal/kg AME | 141 | 414$^{ab}$ | 1,018$^{ab}$ | 1,678$^{ab}$ | 2,474$^{ab}$ | 2,968$^{ab}$ |
| +100 kcal/kg AME | 144 | 421$^a$ | 1,029$^a$ | 1,696$^a$ | 2,495$^a$ | 2,983$^a$ |
| Control diet + amylase | 138 | 397$^c$ | 995$^{bc}$ | 1,664$^{ab}$ | 2,444$^{ab}$ | 2,931$^{ab}$ |
| Mean | 138 | 404 | 1,002 | 1,656 | 2.448 | 2.933 |
| CV, % | 5.13 | 2.35 | 1.73 | 2.34 | 2.46 | 2.18 |
| Probability | 0.1245 | 0.0001 | 0.0001 | 0.0023 | 0.0509 | 0.0363 |

$^{a-c}$Means with different superscript letters differ significantly (P < 0.05) - Tukey test.

TABLE 13

Cumulative feed conversion rate from 1 to 40 days of age, g:g

| Treatments | 1-7 d | 1-14 d | 1-21 d | 1-28 d | 1-35 d | 1-40 d |
|---|---|---|---|---|---|---|
| −100 kcal/kg AME (Control diet) | 1.166$^a$ | 1.300$^a$ | 1.316$^a$ | 1.345$^a$ | 1.450$^a$ | 1.535$^a$ |
| −50 kcal/kg AME | 1.152$^{ab}$ | 1.242$^{abc}$ | 1.299$^a$ | 1.335$^a$ | 1.420$^{abc}$ | 1.518$^{ab}$ |
| Usual levels | 1.167$^a$ | 1.255$^{ab}$ | 1.284$^{ab}$ | 1.309$^{ab}$ | 1.381$^{bc}$ | 1.484$^{bc}$ |
| +50 kcal/kg AME | 1.078$^{ab}$ | 1.209$^{bc}$ | 1.256$^{ab}$ | 1.278$^{bc}$ | 1.374$^{bc}$ | 1.467$^c$ |
| +100 kcal/kg AME | 1.037$^b$ | 1.172$^c$ | 1.232$^c$ | 1.259$^c$ | 1.368$^c$ | 1.453$^c$ |
| Control diet + amylase | 1.149$^{ab}$ | 1.294$^{abc}$ | 1.299$^a$ | 1.321$^{ab}$ | 1.433$^{ab}$ | 1.516$^{ab}$ |
| Mean | 1.128 | 1.240 | 1.286 | 1.313 | 1.413 | 1.501 |
| CV, % | 7.77 | 4.01 | 1.75 | 2.37 | 2.84 | 1.69 |
| Probability | 0.0074 | 0.0001 | 0.0001 | 0.0001 | 0.0001 | 0.0001 |

$^{a-c}$Means with different superscript letters differ significantly (P < 0.05) - Tukey test.

TABLE 14

Regression equations of the evaluated measurements relative to energy level of diets fed to broilers from 1 to 40 d

| Item | Regression Equations[1] | $r^2$ | P-value[2] | Relative bioequivalence[3] Amylase |
|---|---|---|---|---|
| BWG 1-21 d, g | Y = 0.2491x + 980.33 | 0.5010 | 0.0001 | 59 |
| BWG 22-40 d, g | Y = 0.2084x + 1.905 | 0.0840 | 0.0606 | 168 |
| BWG 1-40 d, g | Y = 0.5158x + 2.880 | 0.2654 | 0.0003 | 99 |
| FCR 1-21 d, g | Y = −0.00042x + 1.319 | 0.6851 | 0.0001 | 48 |
| FCR 22-40 d, g | Y = −0.00037x + 1.650 | 0.3413 | 0.0001 | 37 |
| FCR 1-40 d, g | Y = 0.00043x + 1.534 | 0.5494 | 0.0001 | 42 |

[1]Regression equations for energy levels from 1 to 21 d (2.950; 3.000; 3.050; 3.100 and 3.150 kcal/kg) and from 22 to 40 d (3.070; 3.120; 3.170; 3.220 and 3.270 kcal/kg). The coefficient of determination ($r^2$) was obtained using all data.
[2]Linear effect (P < 0.10).
[3]Determined based on response of the means to graded addition of energy for each parameter. Was used the difference between the levels of energy (0, 50, 100, 150 and 200 kcal/kg) to obtain this relative bioequivalence.

In summary, the trials performed well with the addition of the amylase of the invention, especially with respect to improved weight gain and FCR during the grower and finisher phase.

The invention claimed is:

1. A method for improving weight gain and/or feed conversion ratio of poultry, comprising feeding the poultry with a feed which comprises at least one alpha-amylase in an amount of between 20 and 400 KNU/kg feed, wherein the alpha-amylase is a polypeptide having at least 95% identity to amino acids 1-481 of SEQ ID NO: 2 and the alpha-amylase improves weight gain and/or feed conversion ratio of poultry.

2. The method of claim 1, wherein the alpha-amylase has at least 96% identity to amino acids 1-481 of SEQ ID NO: 2.

3. The method of claim 1, wherein the alpha-amylase has at least 97% identity to amino acids 1-481 of SEQ ID NO: 2.

4. The method of claim 1, wherein the alpha-amylase has at least 98% identity to amino acids 1-481 of SEQ ID NO: 2.

5. The method of claim 1, wherein the alpha-amylase has at least 99% identity to amino acids 1-481 of SEQ ID NO: 2.

6. The method of claim 1, wherein the alpha-amylase comprises amino acids 1-481 of SEQ ID NO: 2.

7. The method of claim 1, wherein the poultry feed has reduced apparent metabolisable energy compared to the poultry feed without the alpha-amylase.

8. The method of claim 1, wherein the alpha-amylase is added to the poultry feed at a dose of between 0.01 and 200 mg enzyme protein per kg diet.

* * * * *

SEQUENCE LISTING

<160> NUMBER OF SEQ ID NOS: 9

<210> SEQ ID NO 1
<211> LENGTH: 1620
<212> TYPE: DNA
<213> ORGANISM: Artificial Sequence
<220> FEATURE:
<223> OTHER INFORMATION: Synthetic construct
<220> FEATURE:
<221> NAME/KEY: sig_peptide
<222> LOCATION: (1)..(81)
<220> FEATURE:

<221> NAME/KEY: CDS
<222> LOCATION: (1)..(1620)
<220> FEATURE:
<221> NAME/KEY: mat_peptide
<222> LOCATION: (82)..(1620)

<400> SEQUENCE: 1

```
atg aaa caa caa aaa cgg ctt tac gcc cga ttg ctg acg ctg tta ttt      48
Met Lys Gln Gln Lys Arg Leu Tyr Ala Arg Leu Leu Thr Leu Leu Phe
    -25                 -20                 -15 gcg ctc atc ttc ttg ctg cct cat tct gca gcc gcg gca ccg ttt aac      96
Ala Leu Ile Phe Leu Leu Pro His Ser Ala Ala Ala Pro Phe Asn
-10                  -5                 -1   1               5 ggc acc atg atg cag tat ttt gaa tgg tac ttg ccg gat gat ggc acg     144
Gly Thr Met Met Gln Tyr Phe Glu Trp Tyr Leu Pro Asp Asp Gly Thr
                10                  15                  20 tta tgg acc aaa gtg gcc aat gaa gcc aac aac tta tcc agc ctt ggc     192
Leu Trp Thr Lys Val Ala Asn Glu Ala Asn Asn Leu Ser Ser Leu Gly
             25                  30                  35 atc acc gct ctt tgg ctg ccg ccc gct tac aaa gga aca agc cgc agc     240
Ile Thr Ala Leu Trp Leu Pro Pro Ala Tyr Lys Gly Thr Ser Arg Ser
         40                  45                  50 gac gta ggg tac gga gta tac gac ttg tat gac ctc ggc gaa ttc aat     288
Asp Val Gly Tyr Gly Val Tyr Asp Leu Tyr Asp Leu Gly Glu Phe Asn
     55                  60                  65 caa aaa ggg acc gtc cgc aca aaa tac gga aca aaa gct caa tat ctt     336
Gln Lys Gly Thr Val Arg Thr Lys Tyr Gly Thr Lys Ala Gln Tyr Leu
 70                  75                  80                  85 caa gcc att caa gcc gcc cac gcc gct gga atg caa gtg tac gcc gat     384
Gln Ala Ile Gln Ala Ala His Ala Ala Gly Met Gln Val Tyr Ala Asp
                 90                  95                 100 gtc gtg ttc gac cat aaa ggc ggc gct gac ggc acg gaa tgg gtg gac     432
Val Val Phe Asp His Lys Gly Gly Ala Asp Gly Thr Glu Trp Val Asp
            105                 110                 115 gcc gtc gaa gtc aat ccg tcc gac cgc aac caa gaa atc tcg ggc acc     480
Ala Val Glu Val Asn Pro Ser Asp Arg Asn Gln Glu Ile Ser Gly Thr
        120                 125                 130 tat caa atc caa gca tgg acg aaa ttt gat ttt ccc ggg cgg ggc aac     528
Tyr Gln Ile Gln Ala Trp Thr Lys Phe Asp Phe Pro Gly Arg Gly Asn
135                 140                 145 acc tac tcc agc ttt aag tgg cgc tgg tac cat ttt gac ggc gtt gat     576
Thr Tyr Ser Ser Phe Lys Trp Arg Trp Tyr His Phe Asp Gly Val Asp
150                 155                 160                 165 tgg gac gaa agc cga aaa ttg agc cgc att tac aaa ttc cgt ggc aag     624
Trp Asp Glu Ser Arg Lys Leu Ser Arg Ile Tyr Lys Phe Arg Gly Lys
                170                 175                 180 gct tgg gat tgg gaa gta gac acg gaa ttc gga aac tat gac tac tta     672
Ala Trp Asp Trp Glu Val Asp Thr Glu Phe Gly Asn Tyr Asp Tyr Leu
            185                 190                 195 atg tat gcc gac ctt gat atg gat cat ccc gaa gtc gtg acc gag ctg     720
Met Tyr Ala Asp Leu Asp Met Asp His Pro Glu Val Val Thr Glu Leu
        200                 205                 210 aaa aac tgg ggg aaa tgg tat gtc aac aca acg aac att gat ggg ttc     768
Lys Asn Trp Gly Lys Trp Tyr Val Asn Thr Thr Asn Ile Asp Gly Phe
215                 220                 225 cgg ctt gat gcc gtc aag cat att aag ttc agt ttt ttt cct gat tgg     816
Arg Leu Asp Ala Val Lys His Ile Lys Phe Ser Phe Phe Pro Asp Trp
230                 235                 240                 245 ttg tcg tat gtg cgt tct cag act ggc aag ccg cta ttt acc gtc ggg     864
Leu Ser Tyr Val Arg Ser Gln Thr Gly Lys Pro Leu Phe Thr Val Gly
                250                 255                 260
```

```
gaa tat tgg agc tat gac atc aac aag ttg cac aat tac att acg aaa       912
Glu Tyr Trp Ser Tyr Asp Ile Asn Lys Leu His Asn Tyr Ile Thr Lys
            265                 270                 275 aca gac gga acg atg tct ttg ttt gat gcc ccg tta cac aac aaa ttt       960
Thr Asp Gly Thr Met Ser Leu Phe Asp Ala Pro Leu His Asn Lys Phe
            280                 285                 290 tat acc gct tcc aaa tca ggg ggc gca ttt gat atg cgc acg tta atg      1008
Tyr Thr Ala Ser Lys Ser Gly Gly Ala Phe Asp Met Arg Thr Leu Met
            295                 300                 305 acc aat act ctc atg aaa gat caa ccg aca ttg gcc gtc acc ttc gtt      1056
Thr Asn Thr Leu Met Lys Asp Gln Pro Thr Leu Ala Val Thr Phe Val
310                 315                 320                 325 gat aat cat gac acc gaa ccc ggc caa gcg ctg caa tca tgg gtc gac      1104
Asp Asn His Asp Thr Glu Pro Gly Gln Ala Leu Gln Ser Trp Val Asp
            330                 335                 340 cca tgg ttc aaa ccg ttg gct tac gcc ttt att cta act cgg cag gaa      1152
Pro Trp Phe Lys Pro Leu Ala Tyr Ala Phe Ile Leu Thr Arg Gln Glu
            345                 350                 355 gga tac ccg tgc gtc ttt tat ggt gac tat tat ggc att cca caa tat      1200
Gly Tyr Pro Cys Val Phe Tyr Gly Asp Tyr Tyr Gly Ile Pro Gln Tyr
            360                 365                 370 aac att cct tcg ctg aaa agc aaa atc gat ccg ctc ctc atc gcg cgc      1248
Asn Ile Pro Ser Leu Lys Ser Lys Ile Asp Pro Leu Leu Ile Ala Arg
            375                 380                 385 agg gat tat gct tac gga acg caa cat gat tat ctt gat cac tcc gac      1296
Arg Asp Tyr Ala Tyr Gly Thr Gln His Asp Tyr Leu Asp His Ser Asp
390                 395                 400                 405 atc atc ggg tgg aca agg gaa ggg ggc act gaa aaa cca gga tcc gga      1344
Ile Ile Gly Trp Thr Arg Glu Gly Gly Thr Glu Lys Pro Gly Ser Gly
            410                 415                 420 ctg gcc gca ctg atc acc gat ggg ccg gga gga agc aaa tgg atg tac      1392
Leu Ala Ala Leu Ile Thr Asp Gly Pro Gly Gly Ser Lys Trp Met Tyr
            425                 430                 435 gtt ggc aaa caa cac gct gga aaa gtg ttc tat gac ctt acc ggc aac      1440
Val Gly Lys Gln His Ala Gly Lys Val Phe Tyr Asp Leu Thr Gly Asn
            440                 445                 450 cgg agt gac acc gtc acc atc aac agt gat gga tgg ggg gaa ttc aaa      1488
Arg Ser Asp Thr Val Thr Ile Asn Ser Asp Gly Trp Gly Glu Phe Lys
455                 460                 465 gtc aat ggc ggt tcg gtt tcg gtt tgg gtt cct aga aaa acg acc gtt      1536
Val Asn Gly Gly Ser Val Ser Val Trp Val Pro Arg Lys Thr Thr Val
470                 475                 480                 485 tct acc atc gct cgg ccg atc aca acc cga ccg tgg act ggt gaa ttc      1584
Ser Thr Ile Ala Arg Pro Ile Thr Thr Arg Pro Trp Thr Gly Glu Phe
            490                 495                 500 gtc cgt tgg acc gaa cca cgg ttg gtg gca tgg cct                      1620
Val Arg Trp Thr Glu Pro Arg Leu Val Ala Trp Pro
            505                 510

<210> SEQ ID NO 2
<211> LENGTH: 540
<212> TYPE: PRT
<213> ORGANISM: Artificial Sequence
<220> FEATURE:
<223> OTHER INFORMATION: Synthetic Construct

<400> SEQUENCE: 2

Met Lys Gln Gln Lys Arg Leu Tyr Ala Arg Leu Leu Thr Leu Leu Phe
        -25                 -20                 -15

Ala Leu Ile Phe Leu Leu Pro His Ser Ala Ala Ala Ala Pro Phe Asn
```

```
                -10             -5           -1  1           5
Gly Thr Met Met Gln Tyr Phe Glu Trp Tyr Leu Pro Asp Asp Gly Thr
                    10              15              20

Leu Trp Thr Lys Val Ala Asn Glu Ala Asn Asn Leu Ser Ser Leu Gly
                25              30              35

Ile Thr Ala Leu Trp Leu Pro Pro Ala Tyr Lys Gly Thr Ser Arg Ser
            40              45              50

Asp Val Gly Tyr Gly Val Tyr Asp Leu Tyr Asp Leu Gly Glu Phe Asn
        55              60              65

Gln Lys Gly Thr Val Arg Thr Lys Tyr Gly Thr Lys Ala Gln Tyr Leu
70              75              80              85

Gln Ala Ile Gln Ala Ala His Ala Ala Gly Met Gln Val Tyr Ala Asp
                90              95             100

Val Val Phe Asp His Lys Gly Gly Ala Asp Gly Thr Glu Trp Val Asp
            105             110             115

Ala Val Glu Val Asn Pro Ser Asp Arg Asn Gln Glu Ile Ser Gly Thr
        120             125             130

Tyr Gln Ile Gln Ala Trp Thr Lys Phe Asp Phe Pro Gly Arg Gly Asn
    135             140             145

Thr Tyr Ser Ser Phe Lys Trp Arg Trp Tyr His Phe Asp Gly Val Asp
150             155             160             165

Trp Asp Glu Ser Arg Lys Leu Ser Arg Ile Tyr Lys Phe Arg Gly Lys
                170             175             180

Ala Trp Asp Trp Glu Val Asp Thr Glu Phe Gly Asn Tyr Asp Tyr Leu
            185             190             195

Met Tyr Ala Asp Leu Asp Met Asp His Pro Glu Val Val Thr Glu Leu
        200             205             210

Lys Asn Trp Gly Lys Trp Tyr Val Asn Thr Thr Asn Ile Asp Gly Phe
    215             220             225

Arg Leu Asp Ala Val Lys His Ile Lys Phe Ser Phe Phe Pro Asp Trp
230             235             240             245

Leu Ser Tyr Val Arg Ser Gln Thr Gly Lys Pro Leu Phe Thr Val Gly
                250             255             260

Glu Tyr Trp Ser Tyr Asp Ile Asn Lys Leu His Asn Tyr Ile Thr Lys
            265             270             275

Thr Asp Gly Thr Met Ser Leu Phe Asp Ala Pro Leu His Asn Lys Phe
        280             285             290

Tyr Thr Ala Ser Lys Ser Gly Gly Ala Phe Asp Met Arg Thr Leu Met
    295             300             305

Thr Asn Thr Leu Met Lys Asp Gln Pro Thr Leu Ala Val Thr Phe Val
310             315             320             325

Asp Asn His Asp Thr Glu Pro Gly Gln Ala Leu Gln Ser Trp Val Asp
                330             335             340

Pro Trp Phe Lys Pro Leu Ala Tyr Ala Phe Ile Leu Thr Arg Gln Glu
            345             350             355

Gly Tyr Pro Cys Val Phe Tyr Gly Asp Tyr Tyr Gly Ile Pro Gln Tyr
        360             365             370

Asn Ile Pro Ser Leu Lys Ser Lys Ile Asp Pro Leu Leu Ile Ala Arg
    375             380             385

Arg Asp Tyr Ala Tyr Gly Thr Gln His Asp Tyr Leu Asp His Ser Asp
390             395             400             405

Ile Ile Gly Trp Thr Arg Glu Gly Gly Thr Glu Lys Pro Gly Ser Gly
                410             415             420
```

```
Leu Ala Ala Leu Ile Thr Asp Gly Pro Gly Gly Ser Lys Trp Met Tyr
            425                 430                 435

Val Gly Lys Gln His Ala Gly Lys Val Phe Tyr Asp Leu Thr Gly Asn
        440                 445                 450

Arg Ser Asp Thr Val Thr Ile Asn Ser Asp Gly Trp Gly Glu Phe Lys
    455                 460                 465

Val Asn Gly Gly Ser Val Ser Val Trp Val Pro Arg Lys Thr Val
470                 475                 480                 485

Ser Thr Ile Ala Arg Pro Ile Thr Thr Arg Pro Trp Thr Gly Glu Phe
            490                 495                 500

Val Arg Trp Thr Glu Pro Arg Leu Val Ala Trp Pro
        505                 510

<210> SEQ ID NO 3
<211> LENGTH: 1449
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1449)
<220> FEATURE:
<221> NAME/KEY: mat_peptide
<222> LOCATION: (1)..(1449)

<400> SEQUENCE: 3 cac cat aat ggt acg aac ggc aca atg atg cag tac ttt gaa tgg tat      48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt      96
Leu Pro Asn Asp Gly Asn His Trp Asn Arg Leu Arg Ser Asp Ala Ser
            20                  25                  30 aac cta aaa gat aaa ggg atc tca gcg gtt tgg att cct cct gca tgg     144
Asn Leu Lys Asp Lys Gly Ile Ser Ala Val Trp Ile Pro Pro Ala Trp
        35                  40                  45 aag ggt gcc tct caa aat gat gtg ggg tat ggt gct tat gat ctg tat     192
Lys Gly Ala Ser Gln Asn Asp Val Gly Tyr Gly Ala Tyr Asp Leu Tyr
    50                  55                  60 gat tta gga gaa ttc aat caa aaa gga acc att cgt aca aaa tat gga     240
Asp Leu Gly Glu Phe Asn Gln Lys Gly Thr Ile Arg Thr Lys Tyr Gly
65                  70                  75                  80 acg cgc aat cag tta caa gct gcg gtt aac gcc ttg aaa agt aat gga     288
Thr Arg Asn Gln Leu Gln Ala Ala Val Asn Ala Leu Lys Ser Asn Gly
            85                  90                  95 att caa gtg tat ggc gat gtt gta atg aat cat aaa ggg gga gca gac     336
Ile Gln Val Tyr Gly Asp Val Val Met Asn His Lys Gly Gly Ala Asp
        100                 105                 110 gct acc gaa atg gtt aaa gca gtc gaa gta aac ccg aat aat aga aat     384
Ala Thr Glu Met Val Lys Ala Val Glu Val Asn Pro Asn Asn Arg Asn
    115                 120                 125 caa gaa gtg tcc ggt gaa tat aca att gag gct tgg aca aag ttt gac     432
Gln Glu Val Ser Gly Glu Tyr Thr Ile Glu Ala Trp Thr Lys Phe Asp
130                 135                 140 ttt cca gga cga ggt aat act cat tca aac ttc aaa tgg aga tgg tat     480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga     528
His Phe Asp Gly Val Asp Trp Asp Gln Ser Arg Lys Leu Asn Asn Arg
            165                 170                 175
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| att | tat | aaa | ttc | cgc | ggt | aaa | ggg | tgg | gat | tgg | gaa | gtc | gat | aca | gaa | 576 |
| Ile | Tyr | Lys | Phe | Arg | Gly | Lys | Gly | Trp | Asp | Trp | Glu | Val | Asp | Thr | Glu |     |
|     |     |     |     | 180 |     |     |     | 185 |     |     |     | 190 |     |     |     |     |
| ttc | ggt | aac | tat | gat | tac | cta | atg | tat | gca | gat | att | gac | atg | gat | cac | 624 |
| Phe | Gly | Asn | Tyr | Asp | Tyr | Leu | Met | Tyr | Ala | Asp | Ile | Asp | Met | Asp | His |     |
|     |     |     | 195 |     |     |     | 200 |     |     |     | 205 |     |     |     |     |     |
| cca | gag | gta | gtg | aat | gag | cta | aga | aat | tgg | ggt | gtt | tgg | tat | acg | aat | 672 |
| Pro | Glu | Val | Val | Asn | Glu | Leu | Arg | Asn | Trp | Gly | Val | Trp | Tyr | Thr | Asn |     |
|     | 210 |     |     |     |     | 215 |     |     |     |     | 220 |     |     |     |     |     |
| aca | tta | ggc | ctt | gat | ggt | ttt | aga | ata | gat | gca | gta | aaa | cat | ata | aaa | 720 |
| Thr | Leu | Gly | Leu | Asp | Gly | Phe | Arg | Ile | Asp | Ala | Val | Lys | His | Ile | Lys |     |
| 225 |     |     |     |     | 230 |     |     |     |     | 235 |     |     |     |     | 240 |     |
| tac | agc | ttt | act | cgt | gat | tgg | att | aat | cat | gtt | aga | agt | gca | act | ggc | 768 |
| Tyr | Ser | Phe | Thr | Arg | Asp | Trp | Ile | Asn | His | Val | Arg | Ser | Ala | Thr | Gly |     |
|     |     |     |     | 245 |     |     |     | 250 |     |     |     | 255 |     |     |     |     |
| aaa | aat | atg | ttt | gcg | gtt | gcg | gaa | ttt | tgg | aaa | aat | gat | tta | ggt | gct | 816 |
| Lys | Asn | Met | Phe | Ala | Val | Ala | Glu | Phe | Trp | Lys | Asn | Asp | Leu | Gly | Ala |     |
|     |     | 260 |     |     |     |     | 265 |     |     |     |     | 270 |     |     |     |     |
| att | gaa | aac | tat | tta | aac | aaa | aca | aac | tgg | aac | cat | tca | gtc | ttt | gat | 864 |
| Ile | Glu | Asn | Tyr | Leu | Asn | Lys | Thr | Asn | Trp | Asn | His | Ser | Val | Phe | Asp |     |
|     | 275 |     |     |     |     | 280 |     |     |     |     | 285 |     |     |     |     |     |
| gtt | ccg | ctg | cac | tat | aac | ctc | tat | aat | gct | tca | aaa | agc | gga | ggg | aat | 912 |
| Val | Pro | Leu | His | Tyr | Asn | Leu | Tyr | Asn | Ala | Ser | Lys | Ser | Gly | Gly | Asn |     |
|     | 290 |     |     |     |     | 295 |     |     |     |     | 300 |     |     |     |     |     |
| tat | gat | atg | agg | caa | ata | ttt | aat | ggt | aca | gtc | gtg | caa | aag | cat | cca | 960 |
| Tyr | Asp | Met | Arg | Gln | Ile | Phe | Asn | Gly | Thr | Val | Val | Gln | Lys | His | Pro |     |
| 305 |     |     |     |     | 310 |     |     |     |     | 315 |     |     |     |     | 320 |     |
| atg | cat | gct | gtt | aca | ttt | gtt | gat | aat | cat | gat | tcg | caa | cct | gaa | gaa | 1008 |
| Met | His | Ala | Val | Thr | Phe | Val | Asp | Asn | His | Asp | Ser | Gln | Pro | Glu | Glu |     |
|     |     |     |     | 325 |     |     |     | 330 |     |     |     | 335 |     |     |     |     |
| gct | tta | gag | tct | ttt | gtt | gaa | gaa | tgg | ttc | aaa | cca | tta | gcg | tat | gct | 1056 |
| Ala | Leu | Glu | Ser | Phe | Val | Glu | Glu | Trp | Phe | Lys | Pro | Leu | Ala | Tyr | Ala |     |
|     |     |     | 340 |     |     |     |     | 345 |     |     |     |     | 350 |     |     |     |
| ttg | aca | tta | aca | cgt | gaa | caa | ggc | tac | cct | tct | gta | ttt | tat | gga | gat | 1104 |
| Leu | Thr | Leu | Thr | Arg | Glu | Gln | Gly | Tyr | Pro | Ser | Val | Phe | Tyr | Gly | Asp |     |
|     |     | 355 |     |     |     |     | 360 |     |     |     |     | 365 |     |     |     |     |
| tat | tat | ggc | att | cca | acg | cat | ggt | gta | cca | gcg | atg | aaa | tcg | aaa | att | 1152 |
| Tyr | Tyr | Gly | Ile | Pro | Thr | His | Gly | Val | Pro | Ala | Met | Lys | Ser | Lys | Ile |     |
| 370 |     |     |     |     | 375 |     |     |     |     | 380 |     |     |     |     |     |     |
| gac | ccg | att | cta | gaa | gcg | cgt | caa | aag | tat | gca | tat | gga | aga | caa | aat | 1200 |
| Asp | Pro | Ile | Leu | Glu | Ala | Arg | Gln | Lys | Tyr | Ala | Tyr | Gly | Arg | Gln | Asn |     |
| 385 |     |     |     |     | 390 |     |     |     |     | 395 |     |     |     |     | 400 |     |
| gac | tac | tta | gac | cat | cat | aat | atc | atc | ggt | tgg | aca | cgt | gaa | ggg | aat | 1248 |
| Asp | Tyr | Leu | Asp | His | His | Asn | Ile | Ile | Gly | Trp | Thr | Arg | Glu | Gly | Asn |     |
|     |     |     |     | 405 |     |     |     | 410 |     |     |     | 415 |     |     |     |     |
| aca | gca | cac | ccc | aac | tcc | ggt | tta | gct | act | atc | atg | tcc | gat | ggg | gca | 1296 |
| Thr | Ala | His | Pro | Asn | Ser | Gly | Leu | Ala | Thr | Ile | Met | Ser | Asp | Gly | Ala |     |
|     |     |     | 420 |     |     |     |     | 425 |     |     |     |     | 430 |     |     |     |
| gga | gga | aat | aag | tgg | atg | ttt | gtt | ggg | cgt | aat | aaa | gct | ggt | caa | gtt | 1344 |
| Gly | Gly | Asn | Lys | Trp | Met | Phe | Val | Gly | Arg | Asn | Lys | Ala | Gly | Gln | Val |     |
|     |     | 435 |     |     |     |     | 440 |     |     |     |     | 445 |     |     |     |     |
| tgg | acc | gat | atc | act | gga | aat | aaa | gcc | ggt | act | gtt | acg | att | aat | gct | 1392 |
| Trp | Thr | Asp | Ile | Thr | Gly | Asn | Lys | Ala | Gly | Thr | Val | Thr | Ile | Asn | Ala |     |
|     | 450 |     |     |     |     | 455 |     |     |     |     | 460 |     |     |     |     |     |
| gat | gga | tgg | ggt | aat | ttt | tct | gta | aat | gga | gga | tca | gtt | tct | att | tgg | 1440 |
| Asp | Gly | Trp | Gly | Asn | Phe | Ser | Val | Asn | Gly | Gly | Ser | Val | Ser | Ile | Trp |     |
| 465 |     |     |     |     | 470 |     |     |     |     | 475 |     |     |     |     | 480 |     |
| gta | aac | aaa |     |     |     |     |     |     |     |     |     |     |     |     |     | 1449 |
| Val | Asn | Lys |     |     |     |     |     |     |     |     |     |     |     |     |     |     |

```
<210> SEQ ID NO 4
<211> LENGTH: 483
<212> TYPE: PRT
<213> ORGANISM: Artificial Sequence
<220> FEATURE:
<223> OTHER INFORMATION: Synthetic Construct

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Lys Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Phe Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Val Gln Lys His Pro
305                 310                 315                 320

Met His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365
```

```
Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
            420                 425                 430

Gly Gly Asn Lys Trp Met Phe Val Gly Arg Asn Lys Ala Gly Gln Val
        435                 440                 445

Trp Thr Asp Ile Thr Gly Asn Lys Ala Gly Thr Val Thr Ile Asn Ala
450                 455                 460

Asp Gly Trp Gly Asn Phe Ser Val Asn Gly Ser Val Ser Ile Trp
465                 470                 475                 480

Val Asn Lys

<210> SEQ ID NO 5
<211> LENGTH: 483
<212> TYPE: PRT
<213> ORGANISM: Artificial Sequence
<220> FEATURE:
<223> OTHER INFORMATION: Synthetic construct
<220> FEATURE:
<221> NAME/KEY: mat_peptide
<222> LOCATION: (1)..(483)

<400> SEQUENCE: 5

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Lys Ala Trp Asp Trp Glu Val Asp Ser Glu
            180                 185                 190

Asn Gly Asn Tyr Asp Tyr Leu Met Tyr Ala Asp Val Asp Met Asp His
        195                 200                 205

Pro Glu Val Val Asn Glu Leu Arg Arg Trp Gly Glu Trp Tyr Thr Asn
    210                 215                 220

Thr Leu Asn Leu Asp Gly Phe Arg Ile Asp Ala Val Lys His Ile Lys
```

```
                225                 230                 235                 240
Tyr Ser Phe Thr Arg Asp Trp Leu Thr His Val Arg Asn Ala Thr Gly
                245                 250                 255
Lys Glu Met Phe Ala Val Ala Glu Phe Trp Lys Asn Asp Leu Gly Ala
                260                 265                 270
Leu Glu Asn Tyr Leu Asn Lys Thr Asn Trp Asn His Ser Val Phe Asp
                275                 280                 285
Val Pro Leu His Tyr Asn Leu Tyr Asn Ala Ser Asn Ser Gly Gly Asn
                290                 295                 300
Tyr Asp Met Ala Lys Leu Leu Asn Gly Thr Val Val Gln Lys His Pro
305                 310                 315                 320
Met His Ala Val Thr Phe Val Asp Asn His Asp Ser Gln Pro Gly Glu
                325                 330                 335
Ser Leu Glu Ser Phe Val Gln Glu Trp Phe Lys Pro Leu Ala Tyr Ala
                340                 345                 350
Leu Ile Leu Thr Arg Glu Gln Gly Tyr Pro Ser Val Phe Tyr Gly Asp
                355                 360                 365
Tyr Tyr Gly Ile Pro Thr His Ser Val Pro Ala Met Lys Ala Lys Ile
                370                 375                 380
Asp Pro Ile Leu Glu Ala Arg Gln Asn Phe Ala Tyr Gly Thr Gln His
385                 390                 395                 400
Asp Tyr Phe Asp His His Asn Ile Ile Gly Trp Thr Arg Glu Gly Asn
                405                 410                 415
Thr Thr His Pro Asn Ser Gly Leu Ala Thr Ile Met Ser Asp Gly Pro
                420                 425                 430
Gly Gly Glu Lys Trp Met Tyr Val Gly Gln Asn Lys Ala Gly Gln Val
                435                 440                 445
Trp His Asp Ile Thr Gly Asn Lys Pro Gly Thr Val Thr Ile Asn Ala
                450                 455                 460
Asp Gly Trp Ala Asn Phe Ser Val Asn Gly Gly Ser Val Ser Ile Trp
465                 470                 475                 480

Val Lys Arg

<210> SEQ ID NO 6
<211> LENGTH: 510
<212> TYPE: PRT
<213> ORGANISM: Artificial Sequence
<220> FEATURE:
<223> OTHER INFORMATION: Synthetic construct
<220> FEATURE:
<221> NAME/KEY: SIGNAL
<222> LOCATION: (1)..(29)
<220> FEATURE:
<221> NAME/KEY: mat_peptide
<222> LOCATION: (30)..(510)

<400> SEQUENCE: 6

Met Lys Gln Gln Lys Arg Leu Tyr Ala Arg Leu Leu Thr Leu Leu Phe
                -25                 -20                 -15
Ala Leu Ile Phe Leu Leu Pro His Ser Ala Ala Ala Val Asn Gly
                -10                 -5                  -1   1
Thr Leu Met Gln Tyr Phe Glu Trp Tyr Thr Pro Asn Asp Gly Gln His
  5                  10                  15
Trp Lys Arg Leu Gln Asn Asp Ala Glu His Leu Ser Asp Ile Gly Ile
 20                  25                  30                  35
Thr Ala Val Trp Ile Pro Pro Ala Tyr Lys Gly Thr Ser Gln Ala Asp
                 40                  45                  50
```

```
Val Gly Tyr Gly Ala Tyr Asp Leu Tyr Asp Leu Gly Glu Phe His Gln
            55                  60                  65
Lys Gly Thr Val Arg Thr Lys Tyr Gly Thr Lys Gly Glu Leu Gln Ser
        70                  75                  80
Ala Ile Lys Ser Leu His Ser Arg Asp Ile Asn Val Tyr Gly Asp Val
    85                  90                  95
Val Ile Asn His Lys Gly Gly Ala Asp Ala Thr Glu Asp Val Thr Ala
100                 105                 110                 115
Val Glu Val Asp Pro Ala Asp Arg Asn Arg Val Ile Ser Gly Glu His
                120                 125                 130
Leu Ile Lys Ala Trp Thr His Phe His Phe Pro Gly Arg Gly Ser Thr
            135                 140                 145
Tyr Ser Asp Phe Lys Trp His Trp Tyr His Phe Asp Gly Thr Asp Trp
        150                 155                 160
Asp Glu Ser Arg Lys Leu Asn Arg Ile Tyr Lys Phe Gln Gly Lys Ala
    165                 170                 175
Trp Asp Trp Glu Val Ser Asn Glu Asn Gly Asn Tyr Asp Tyr Leu Thr
180                 185                 190                 195
Tyr Ala Asp Ile Asp Tyr Asp His Pro Asp Val Ala Ala Glu Ile Lys
                200                 205                 210
Arg Trp Gly Thr Trp Tyr Ala Asn Glu Leu Gln Leu Asp Gly Phe Arg
            215                 220                 225
Leu Asp Ala Val Lys His Ile Lys Phe Ser Phe Leu Arg Asp Trp Val
        230                 235                 240
Asn His Val Arg Glu Lys Thr Gly Lys Glu Met Phe Thr Val Ala Glu
    245                 250                 255
Tyr Trp Gln Asn Asp Leu Gly Ala Leu Glu Asn Tyr Leu Asn Lys Thr
260                 265                 270                 275
Asn Phe Asn His Ser Val Phe Asp Val Pro Leu His Tyr Gln Phe His
                280                 285                 290
Ala Ala Ser Thr Gln Gly Gly Tyr Asp Met Arg Lys Leu Leu Asn
            295                 300                 305
Gly Thr Val Val Ser Lys His Pro Leu Lys Ser Val Thr Phe Val Asp
        310                 315                 320
Asn His Asp Thr Gln Pro Gly Gln Ser Leu Glu Ser Thr Val Gln Thr
    325                 330                 335
Trp Phe Lys Pro Leu Ala Tyr Ala Phe Ile Leu Thr Arg Glu Ser Gly
340                 345                 350                 355
Tyr Pro Gln Val Phe Tyr Gly Asp Met Tyr Gly Thr Lys Gly Asp Ser
                360                 365                 370
Gln Arg Glu Ile Pro Ala Leu Lys His Lys Ile Glu Pro Ile Leu Lys
            375                 380                 385
Ala Arg Lys Gln Tyr Ala Tyr Gly Ala Gln His Asp Tyr Phe Asp His
        390                 395                 400
His Asp Ile Val Gly Trp Thr Arg Glu Gly Asp Ser Ser Val Ala Asn
    405                 410                 415
Ser Gly Leu Ala Ala Leu Ile Thr Asp Gly Pro Gly Gly Ala Lys Arg
420                 425                 430                 435
Met Tyr Val Gly Arg Gln Asn Ala Gly Glu Thr Trp His Asp Ile Thr
                440                 445                 450
Gly Asn Arg Ser Glu Pro Val Val Ile Asn Ser Glu Gly Trp Gly Glu
            455                 460                 465
```

```
Phe His Val Asn Gly Gly Ser Val Ser Ile Tyr Val Gln Arg
            470                 475                 480

<210> SEQ ID NO 7
<211> LENGTH: 514
<212> TYPE: PRT
<213> ORGANISM: Bacillus amyloliquefaciens
<220> FEATURE:
<221> NAME/KEY: SIGNAL
<222> LOCATION: (1)..(31)
<220> FEATURE:
<221> NAME/KEY: mat_peptide
<222> LOCATION: (32)..(514)

<400> SEQUENCE: 7

Met Ile Gln Lys Arg Lys Arg Thr Val Ser Phe Arg Leu Val Leu Met
    -30                 -25                 -20

Cys Thr Leu Leu Phe Val Ser Leu Pro Ile Thr Lys Thr Ser Ala Val
-15                 -10                  -5                  -1  1

Asn Gly Thr Leu Met Gln Tyr Phe Glu Trp Tyr Thr Pro Asn Asp Gly
                  5                  10                  15

Gln His Trp Lys Arg Leu Gln Asn Asp Ala Glu His Leu Ser Asp Ile
             20                  25                  30

Gly Ile Thr Ala Val Trp Ile Pro Pro Ala Tyr Lys Gly Leu Ser Gln
         35                  40                  45

Ser Asp Asn Gly Tyr Gly Pro Tyr Asp Leu Tyr Asp Leu Gly Glu Phe
50                   55                  60                  65

Gln Gln Lys Gly Thr Val Arg Thr Lys Tyr Gly Thr Lys Ser Glu Leu
                 70                  75                  80

Gln Asp Ala Ile Gly Ser Leu His Ser Arg Asn Val Gln Val Tyr Gly
             85                  90                  95

Asp Val Val Leu Asn His Lys Ala Gly Ala Asp Ala Thr Glu Asp Val
            100                 105                 110

Thr Ala Val Glu Val Asn Pro Ala Asn Arg Asn Gln Glu Thr Ser Glu
115                 120                 125

Glu Tyr Gln Ile Lys Ala Trp Thr Asp Phe Arg Phe Pro Gly Arg Gly
130                 135                 140                 145

Asn Thr Tyr Ser Asp Phe Lys Trp His Trp Tyr His Phe Asp Gly Ala
                150                 155                 160

Asp Trp Asp Glu Ser Arg Lys Ile Ser Arg Ile Phe Lys Phe Arg Gly
            165                 170                 175

Glu Gly Lys Ala Trp Asp Trp Glu Val Ser Ser Glu Asn Gly Asn Tyr
            180                 185                 190

Asp Tyr Leu Met Tyr Ala Asp Val Asp Tyr Asp His Pro Asp Val Val
        195                 200                 205

Ala Glu Thr Lys Lys Trp Gly Ile Trp Tyr Ala Asn Glu Leu Ser Leu
210                 215                 220                 225

Asp Gly Phe Arg Ile Asp Ala Ala Lys His Ile Lys Phe Ser Phe Leu
                230                 235                 240

Arg Asp Trp Val Gln Ala Val Arg Gln Ala Thr Gly Lys Glu Met Phe
                245                 250                 255

Thr Val Ala Glu Tyr Trp Gln Asn Asn Ala Gly Lys Leu Glu Asn Tyr
            260                 265                 270

Leu Asn Lys Thr Ser Phe Asn Gln Ser Val Phe Asp Val Pro Leu His
        275                 280                 285

Phe Asn Leu Gln Ala Ala Ser Ser Gln Gly Gly Gly Tyr Asp Met Arg
290                 295                 300                 305
```

```
Arg Leu Leu Asp Gly Thr Val Val Ser Arg His Pro Glu Lys Ala Val
                310                 315                 320

Thr Phe Val Glu Asn His Asp Thr Gln Pro Gly Gln Ser Leu Glu Ser
            325                 330                 335

Thr Val Gln Thr Trp Phe Lys Pro Leu Ala Tyr Ala Phe Ile Leu Thr
        340                 345                 350

Arg Glu Ser Gly Tyr Pro Gln Val Phe Tyr Gly Asp Met Tyr Gly Thr
    355                 360                 365

Lys Gly Thr Ser Pro Lys Glu Ile Pro Ser Leu Lys Asp Asn Ile Glu
370                 375                 380                 385

Pro Ile Leu Lys Ala Arg Lys Glu Tyr Ala Tyr Gly Pro Gln His Asp
                390                 395                 400

Tyr Ile Asp His Pro Asp Val Ile Gly Trp Thr Arg Glu Gly Asp Ser
            405                 410                 415

Ser Ala Ala Lys Ser Gly Leu Ala Ala Leu Ile Thr Asp Gly Pro Gly
        420                 425                 430

Gly Ser Lys Arg Met Tyr Ala Gly Leu Lys Asn Ala Gly Glu Thr Trp
    435                 440                 445

Tyr Asp Ile Thr Gly Asn Arg Ser Asp Thr Val Lys Ile Gly Ser Asp
450                 455                 460                 465

Gly Trp Gly Glu Phe His Val Asn Asp Gly Ser Val Ser Ile Tyr Val
                470                 475                 480

Gln Lys

<210> SEQ ID NO 8
<211> LENGTH: 512
<212> TYPE: PRT
<213> ORGANISM: Bacillus licheniformis
<220> FEATURE:
<221> NAME/KEY: SIGNAL
<222> LOCATION: (1)..(29)
<220> FEATURE:
<221> NAME/KEY: mat_peptide
<222> LOCATION: (30)..(512)

<400> SEQUENCE: 8

Met Lys Gln Gln Lys Arg Leu Tyr Ala Arg Leu Leu Thr Leu Leu Phe
                -25                 -20                 -15

Ala Leu Ile Phe Leu Leu Pro His Ser Ala Ala Ala Ala Asn Leu
            -10                  -5              -1   1

Asn Gly Thr Leu Met Gln Tyr Phe Glu Trp Tyr Met Pro Asn Asp Gly
  5                  10                  15

Gln His Trp Lys Arg Leu Gln Asn Asp Ser Ala Tyr Leu Ala Glu His
20                  25                  30                  35

Gly Ile Thr Ala Val Trp Ile Pro Pro Ala Tyr Lys Gly Thr Ser Gln
                40                  45                  50

Ala Asp Val Gly Tyr Gly Ala Tyr Asp Leu Tyr Asp Leu Gly Glu Phe
            55                  60                  65

His Gln Lys Gly Thr Val Arg Thr Lys Tyr Gly Thr Lys Gly Glu Leu
        70                  75                  80

Gln Ser Ala Ile Lys Ser Leu His Ser Arg Asp Ile Asn Val Tyr Gly
    85                  90                  95

Asp Val Val Ile Asn His Lys Gly Gly Ala Asp Ala Thr Glu Asp Val
100                 105                 110                 115

Thr Ala Val Glu Val Asp Pro Ala Asp Arg Asn Arg Val Ile Ser Gly
                120                 125                 130
```

```
Glu His Arg Ile Lys Ala Trp Thr His Phe His Phe Pro Gly Arg Gly
            135                 140                 145
Ser Thr Tyr Ser Asp Phe Lys Trp His Trp Tyr His Phe Asp Gly Thr
            150                 155                 160
Asp Trp Asp Glu Ser Arg Lys Leu Asn Arg Ile Tyr Lys Phe Gln Gly
165                 170                 175
Lys Ala Trp Asp Trp Glu Val Ser Asn Glu Asn Gly Asn Tyr Asp Tyr
180                 185                 190                 195
Leu Met Tyr Ala Asp Ile Asp Tyr Asp His Pro Asp Val Ala Ala Glu
                200                 205                 210
Ile Lys Arg Trp Gly Thr Trp Tyr Ala Asn Glu Leu Gln Leu Asp Gly
            215                 220                 225
Phe Arg Leu Asp Ala Val Lys His Ile Lys Phe Ser Phe Leu Arg Asp
            230                 235                 240
Trp Val Asn His Val Arg Glu Lys Thr Gly Lys Glu Met Phe Thr Val
            245                 250                 255
Ala Glu Tyr Trp Gln Asn Asp Leu Gly Ala Leu Glu Asn Tyr Leu Asn
260                 265                 270                 275
Lys Thr Asn Phe Asn His Ser Val Phe Asp Val Pro Leu His Tyr Gln
                280                 285                 290
Phe His Ala Ala Ser Thr Gln Gly Gly Gly Tyr Asp Met Arg Lys Leu
            295                 300                 305
Leu Asn Ser Thr Val Val Ser Lys His Pro Leu Lys Ala Val Thr Phe
            310                 315                 320
Val Asp Asn His Asp Thr Gln Pro Gly Gln Ser Leu Glu Ser Thr Val
            325                 330                 335
Gln Thr Trp Phe Lys Pro Leu Ala Tyr Ala Phe Ile Leu Thr Arg Glu
340                 345                 350                 355
Ser Gly Tyr Pro Gln Val Phe Tyr Gly Asp Met Tyr Gly Thr Lys Gly
                360                 365                 370
Asp Ser Gln Arg Glu Ile Pro Ala Leu Lys His Lys Ile Glu Pro Ile
            375                 380                 385
Leu Lys Ala Arg Lys Gln Tyr Ala Tyr Gly Ala Gln His Asp Tyr Phe
            390                 395                 400
Asp His His Asp Ile Val Gly Trp Thr Arg Glu Gly Asp Ser Ser Val
            405                 410                 415
Ala Asn Ser Gly Leu Ala Ala Leu Ile Thr Asp Gly Pro Gly Gly Ala
420                 425                 430                 435
Lys Arg Met Tyr Val Gly Arg Gln Asn Ala Gly Glu Thr Trp His Asp
                440                 445                 450
Ile Thr Gly Asn Arg Ser Glu Pro Val Val Ile Asn Ser Glu Gly Trp
            455                 460                 465
Gly Glu Phe His Val Asn Gly Gly Ser Val Ser Ile Tyr Val Gln Arg
            470                 475                 480

<210> SEQ ID NO 9
<211> LENGTH: 549
<212> TYPE: PRT
<213> ORGANISM: Bacillus stearothermophilus
<220> FEATURE:
<221> NAME/KEY: SIGNAL
<222> LOCATION: (1)..(34)
<220> FEATURE:
<221> NAME/KEY: mat_peptide
<222> LOCATION: (35)..(549)
```

<400> SEQUENCE: 9

```
Met Leu Thr Phe His Arg Ile Ile Arg Lys Gly Trp Met Phe Leu Leu
            -30                 -25                 -20
Ala Phe Leu Leu Thr Ala Leu Leu Phe Cys Pro Thr Gly Gln Pro Ala
            -15                 -10                  -5
Lys Ala Ala Ala Pro Phe Asn Gly Thr Met Met Gln Tyr Phe Glu Trp
 -1   1               5                  10
Tyr Leu Pro Asp Asp Gly Thr Leu Trp Thr Lys Val Ala Asn Glu Ala
 15              20                  25                  30
Asn Asn Leu Ser Ser Leu Gly Ile Thr Ala Leu Trp Leu Pro Pro Ala
                 35                  40                  45
Tyr Lys Gly Thr Ser Arg Ser Asp Val Gly Tyr Gly Val Tyr Asp Leu
             50                  55                  60
Tyr Asp Leu Gly Glu Phe Asn Gln Lys Gly Ala Val Arg Thr Lys Tyr
             65                  70                  75
Gly Thr Lys Ala Gln Tyr Leu Gln Ala Ile Gln Ala Ala His Ala Ala
     80                  85                  90
Gly Met Gln Val Tyr Ala Asp Val Val Phe Asp His Lys Gly Gly Ala
 95                 100                 105                 110
Asp Gly Thr Glu Trp Val Asp Ala Val Glu Val Asn Pro Ser Asp Arg
                115                 120                 125
Asn Gln Glu Ile Ser Gly Thr Tyr Gln Ile Gln Ala Trp Thr Lys Phe
            130                 135                 140
Asp Phe Pro Gly Arg Gly Asn Thr Tyr Ser Ser Phe Lys Trp Arg Trp
            145                 150                 155
Tyr His Phe Asp Gly Val Asp Trp Asp Glu Ser Arg Lys Leu Ser Arg
            160                 165                 170
Ile Tyr Lys Phe Arg Gly Ile Gly Lys Ala Trp Asp Trp Glu Val Asp
175                 180                 185                 190
Thr Glu Asn Gly Asn Tyr Asp Tyr Leu Met Tyr Ala Asp Leu Asp Met
                195                 200                 205
Asp His Pro Glu Val Val Thr Glu Leu Lys Ser Trp Gly Lys Trp Tyr
            210                 215                 220
Val Asn Thr Thr Asn Ile Asp Gly Phe Arg Leu Asp Ala Val Lys His
            225                 230                 235
Ile Lys Phe Ser Phe Pro Asp Trp Leu Ser Asp Val Arg Ser Gln
240                 245                 250
Thr Gly Lys Pro Leu Phe Thr Val Gly Glu Tyr Trp Ser Tyr Asp Ile
255                 260                 265                 270
Asn Lys Leu His Asn Tyr Ile Met Lys Thr Asn Gly Thr Met Ser Leu
                275                 280                 285
Phe Asp Ala Pro Leu His Asn Lys Phe Tyr Thr Ala Ser Lys Ser Gly
            290                 295                 300
Gly Thr Phe Asp Met Arg Thr Leu Met Thr Asn Thr Leu Met Lys Asp
            305                 310                 315
Gln Pro Thr Leu Ala Val Thr Phe Val Asp Asn His Asp Thr Glu Pro
            320                 325                 330
Gly Gln Ala Leu Gln Ser Trp Val Asp Pro Trp Phe Lys Pro Leu Ala
335                 340                 345                 350
Tyr Ala Phe Ile Leu Thr Arg Gln Glu Gly Tyr Pro Cys Val Phe Tyr
                355                 360                 365
Gly Asp Tyr Tyr Gly Ile Pro Gln Tyr Asn Ile Pro Ser Leu Lys Ser
            370                 375                 380
```

-continued

```
Lys Ile Asp Pro Leu Leu Ile Ala Arg Arg Asp Tyr Ala Tyr Gly Thr
        385                 390                 395

Gln His Asp Tyr Leu Asp His Ser Asp Ile Ile Gly Trp Thr Arg Glu
    400                 405                 410

Gly Val Thr Glu Lys Pro Gly Ser Gly Leu Ala Ala Leu Ile Thr Asp
415                 420                 425                 430

Gly Pro Gly Gly Ser Lys Trp Met Tyr Val Gly Lys Gln His Ala Gly
                435                 440                 445

Lys Val Phe Tyr Asp Leu Thr Gly Asn Arg Ser Asp Thr Val Thr Ile
            450                 455                 460

Asn Ser Asp Gly Trp Gly Glu Phe Lys Val Asn Gly Gly Ser Val Ser
        465                 470                 475

Val Trp Val Pro Arg Lys Thr Thr Val Ser Thr Ile Ala Trp Ser Ile
    480                 485                 490

Thr Thr Arg Pro Trp Thr Asp Glu Phe Val Arg Trp Thr Glu Pro Arg
495                 500                 505                 510

Leu Val Ala Trp Pro
                515
```